United States Patent
Bavetsias et al.

(10) Patent No.: US 7,528,141 B2
(45) Date of Patent: May 5, 2009

(54) USE OF CYCLOPENTA[G]QUINAZOLINE DERIVATIVES FOR TREATING CANCER

(75) Inventors: Vasilios Bavetsias, Sutton (GB); Ann L Jackman, Horsham (GB)

(73) Assignee: BTG International Limited, London (GB)

( * ) Notice: Subject to any disclaimer, the term of this patent is extended or adjusted under 35 U.S.C. 154(b) by 34 days.

(21) Appl. No.: 10/487,874

(22) PCT Filed: Aug. 30, 2002

(86) PCT No.: PCT/GB02/03961

§ 371 (c)(1),
(2), (4) Date: Aug. 23, 2004

(87) PCT Pub. No.: WO03/020300

PCT Pub. Date: Mar. 13, 2003

(65) Prior Publication Data

US 2005/0009851 A1    Jan. 13, 2005

Related U.S. Application Data

(60) Provisional application No. 60/340,243, filed on Dec. 18, 2001.

(30) Foreign Application Priority Data

| Aug. 31, 2001 | (GB) | ................................ 0121151.5 |
| Aug. 31, 2001 | (GB) | ................................ 0121214.1 |
| Dec. 7, 2001 | (GB) | ................................ 0129388.5 |

(51) Int. Cl.
*A61K 31/505* (2006.01)
(52) U.S. Cl. .................................................. 514/267
(58) Field of Classification Search ................ 514/267, 514/249
See application file for complete search history.

(56) References Cited

U.S. PATENT DOCUMENTS 5,747,499 A * 5/1998 Bavetsias et al. ............. 514/267

OTHER PUBLICATIONS

Bavetsias, V. et al. Design and Synthesis of Cyclopenta[g]quinazoline-Based Antifolates as Inhibitors of Thymidylate Synthase and Potential Antitumor Agents. J. Med. Chem., 2000, 43, 1910-1926.*
Sausville et al. Cancer Research, 2006, vol. 66, pp. 3351-3354.*
Johnson et al. British J. of Cancer, 2001, 84(10):1424-1431.*
Campbell, I.G., et al; "Folate-binding Protein Is a Marker for Ovarian Cancer"; *Cancer Research*; 51, pp. 5329-5338 (Oct. 1991).

* cited by examiner

*Primary Examiner*—Ardin Marschel
*Assistant Examiner*—James D Anderson
(74) *Attorney, Agent, or Firm*—Nixon & Vanderhye

(57) ABSTRACT

Method for aiding regression and palliation of a solid tumor in a patient in need of such treatment, comprising administering to the patient an effective amount of a cyclopenta[g]quinazoline of the formula (I) as set forth in the specification, wherein A is hydrogen or a group OR or $NR^0R^1$ wherein $R^0$ and $R^1$ are each independently hydrogen $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring; p is an integer in the range 1 to 4; $R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl; $Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group the formula $-A^5-CON(R)CH(Y^4)Y^5$, and pharmaceutically acceptable salts or esters.

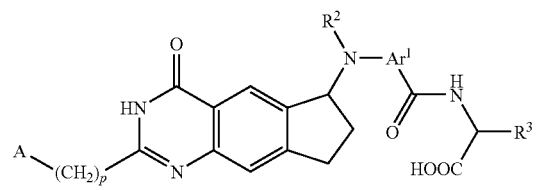

(I)

4 Claims, No Drawings

USE OF CYCLOPENTA[G]QUINAZOLINE DERIVATIVES FOR TREATING CANCER

This application is the U.S. National Phase of International Application PCT/GB2002/03961, filed 30 Aug. 2002, which designated the U.S. PCT/GB2002/03961 claims priority to British Application No. 0121214.1 filed 31 Aug. 2001, British Application No. 0121151.5 filed 31 Aug. 2001, British Application No. 0129388.5 filed 7 Dec. 2001 and Provisional Application No. 60/340,243 filed 18 Dec. 2001. The entire contents of these applications are incorporated herein by reference.

This invention relates to the use of compounds as anticancer agents. More particularly it relates to cyclopenta[g]quinazoline derivatives which possess antiproliferative activity in the treatment of solid tumours.

One group of anti-cancer agents comprises antimetabolites having antifolate activity, such as the dihydrofolate reductase inhibitor, methotrexate and the thymidylate synthase (TS) inhibitors CB3717, raltitrexed and ZD9331. CB3717 is described and claimed in EP-B-0031237, raltitrexed in EP-B-0239362 and ZD9331 in EP-B-0562734. All of these TS inhibitors have demonstrable clinical activity in a range of solid tumours (see Cancer Treatment Reports, 1986, 70, 1335 and Beale et al., "Tomudex: Clinical Development" in Antifolate Drugs in Cancer Therapy (ed. Jackman), Humana Press, Totowa, N.J., USA, pp. 177-181, 1999). Side-effects of raltitrexed and ZD9331 are predominantly related to inhibition of TS in gut and bone-marrow.

TS catalyses the methylation of deoxyuridine monophosphate to produce thymidine monophosphate which is required for DNA synthesis. The anticancer activity of these agents may be assessed in vitro by determining their inhibitory effect on that enzyme, and in cell cultures by their inhibitory effect on a range of mouse and human cancer cell lines (see Boyle et al, "ZD9331: Preclinical and clinical studies" in Antifolate Drugs in Cancer Therapy (ed. Jackman), Humana Press, Totowa, N.J., USA, pp. 243-260, 1999 and Hughes et al., "Raltitrexed (Tomudex), a highly polyglutamatable antifolate thymidylate synthase inhibitor: design and preclinical activity" in Antifolate Drugs in Cancer Therapy (ed. Jackman), Humana Press, Totowa, N.J., USA, pp. 147-165, 1999).

More recently, cyclopenta[g]quinazoline derivatives showing a good level of activity both as regards their ability to inhibit TS and also as regards their anticancer activity against various cell lines have been developed.

WO-A-94/11354 (British Technology Group Limited) discloses tricyclic compound of formula:

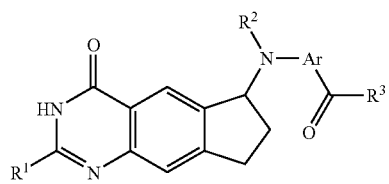

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

$R^2$ is hydrogen, $C_{1-4}$ alkyl, $C_{3-4}$ alkenyl, $C_{3-4}$ alkynyl, $C_{2-4}$ A hydroxyalkyl $C_{2-4}$ halogenoalkyl or $C_{1-4}$ cyanoalkyl;

Ar is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of one of the following formulae:

—NHCH(CO$_2$H)-A$^1$—Y$^1$—NH-A$^3$-Y$^3$

or $R^3$ is a N-linked naturally-occurring amino acid selected from the group consisting of L-alanine, L-leucine, L-isoleucine, L-valine and L-phenylalanine. Among the compounds disclosed is the L-Glu-γ-D-Glu compound CB300638, also mentioned in Clinical Cancer Research, 5, November 1999 (Supplement) at #566 (Theti et al.) and Proceedings of the American Association for Cancer Research, 41, March 2000 at #33 (Jackman et al.), as well as in J. Med. Chem., 2000, 43, 1910-1926, where it is disclosed on page 1923 as compound 7b.

WO-A-95/30673 (British Technology Group Limited) discloses cyclopenta-[g]quinazolines of formula:

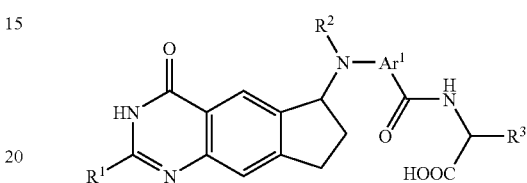

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

$R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

Ar$^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of one of the following formulae:

-A$^1$-Ar$^2$-A$^2$-Y$^1$ -A-CON(R)CH(Y$^4$)Y$^5$ -A$^8$-X—Ar$^4$

The α-isoform of the folate receptor (α-FR; membrane-associated folate-binding protein) is a glycosylphosphatidylinositol anchored cell membrane protein that has very high affinity for folic acid and the more biologically relevant reduced-folates (Kd~0.1 nM). The mechanism of folate internalisation is receptor-mediated endocytosis. The α-FR is overexpressed in many carcinomas, particularly those of ovarian origin where it is overexpressed highly and homogeneously in 90% of cases; see Cancer Res. 51, 5329-5338, 1991 (Campbell et al, 1991). Furthermore, high α-FR expression has been linked to aggressive, platinum resistant disease and poor prognosis—see Int. J. Cancer 74, 193-198, 1997 and Int. J. Cancer 79, 121-126, 1998 both Toffoli et al.). The β-isoform is widely expressed in tumours of epithelial and non-epithelial origin with expression levels being generally low/moderate and high, respectively, reviewed in Critical Rev. Therap. in Drug Carrier Systems 15, 587-627, 1998 (Reddy and Low).

Polate receptors (α and β) are expressed in some adult normal tissues (low to moderate expression). Significant expression of the α-FR is largely restricted to kidney proximal tubules and choroid plexus although it is suggested that it is localised to the apical membrane surface in these organs and therefore may not play a significant role in folate uptake from blood (Reddy and Low, ibid.). There may be a specialised function of the α-FR in the proximal tubules of the kidney to salvage folates that escape in the filtrate.

The α-FR is hypothesised to be involved in cell signalling pathways. For example, in IGROV-1 ovarian carcinoma cells, immunoprecipitation experiments have shown that the α-FR is associated in membranes with the G protein $G_{α1-3}$, and the non-receptor kinase lyn.

High FR expression in some tumours relative to normal tissues is being exploited in several areas of cancer medicine, including the selective tumour delivery of conjugates of folic acid and toxins, liposomes, imaging or cytotoxic agents (Reddy and Low, ibid.). For example, folic acid-deferroxamine-$^{III}$In conjugates are detected only in FR-expressing tumours and not normal tissues of mice, with the exception of kidney epithelial cells. The high selectivity of this approach resides in the very low and high affinities of folic acid (not a major component of plasma) for the RFC (reduced-folate carrier) and FR respectively. Thus antifolate drugs with similarly low and high affinity for the RFC and α-FR respectively could be highly selective for α-FR over-expressing tumours relative to normal tissues. In contrast with the folic acid conjugates they would not require intracellular cleavage to be active.

We have now discovered that certain compounds within the general class of cyclopenta[g]quinazolines have an unexpectedly high level of selectivity for α-folate receptor expressing human tumour cell lines. Accordingly the present invention comprises the use of a cyclopenta[g]quinazoline of formula (I):

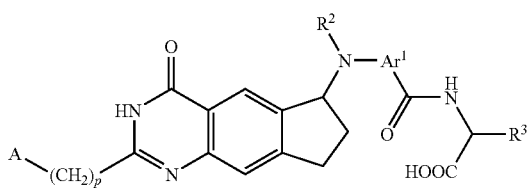

wherein:

A is hydrogen or a group $OR^0$ or $NR^0R^1$ wherein $R^0$ and $R^1$ are each independently hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring;

p is an integer in the range 1 to 4;

$R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of the formula:

-$A^5$-CON(R)CH($Y^4$)$Y^5$ in which $A^5$ is a $C_{1-6}$ alkylene group and R is hydrogen, $C_{1-4}$ alkyl, $C_{3-4}$ alkenyl or $C_{3-4}$ alkynyl;

$Y^4$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^5$ is the residue of a naturally occurring amino acid $NH_2CH(CO_2H)Y^5$; or $Y^5$ is a group of the formula:

-$A^4$-$CO_2H$ in which $A^4$ is a $C_{2-6}$ alkylene group; or $Y^5$ is a group of the formula:

-$A^6$-$Ar^3$-$A^7$-$Y^6$ in which $A^6$ is a bond between the α-carbon atom of the group -$A^5$-CON(R)CH($Y^4$)— and $Ar^3$ or is a $C_{1-2}$ alkylene group;

$Ar^3$ is phenylene, tetrazolediyl, thiophenedlyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy, $A^7$ is a $C_{1-3}$ alkylene or $C_{2-3}$ alkenylene group; and $Y^6$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl;

the compound (I) optionally being in the form of a pharmaceutically acceptable salt or ester;

for the manufacture of a medicament for the treatment of solid tumours.

The compounds of the invention display one or more of the following advantages:

1. They have high selectivity for tumours over-expressing the α-FR, when grown in physiological concentrations of folate and possessing normal expression of the RFC.
2. They display a potent TS inhibition, a low affinity for the RFC and a moderate to high affinity for the α-FR (inverse relative affinity of approx. 0.1 to 1.5).
3. They have TS-specific activity and are resistant to in vivo hydrolases.
4. They display selective activity (in the order of >100-fold) in primary human cell line screen with high α-FR expression (A431/A431-FBP isogenic pair and KB cells=folic acid). They display selective activity (in the order of >10-fold) in cell lines with moderate FR expression. They display tumour-specific localisation in mice. They display antitumour activity in xenografts with no toxicity.

In this specification the terms alkyl, alkenyl, alkynyl and alkylene include both straight and branched chain groups but references to individual alkyl or alkylene groups, such as "propyl", are specific for the straight chain group only. An analogous convention applies to other generic terns. Moreover, the numbering system used for the cyclopenta[g]quinazoline nucleus is the conventional one as shown below:

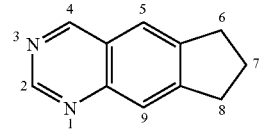

Amino-acid residues are designated herein in the standard manner (*Pure and Applied Chemistry*, 1974, 40, 317 and *European Journal of Biochemistry*, 1984, 138, 9). Thus, for example, γ-glutamyl denotes the radical $H_2NCH(CO_2H)CH_2CH_2CO$— or —$NHCH(CO_2H)CH_2CH_2CO$— according to the context, the carbon atoms in these radicals being numbered from the carbon atom of the α-carboxy group as position 1.

It will be observed that a cyclopenta[g]quinazoline of the invention contains at least two asymmetric carbon atoms [present at the point of attachment of the group —N($R^2$)— to the tricyclic ring system and at the α-carbon atom of the group —CONHCH($CO_2H$)—] and can therefore exist in racemic and optically active forms. It is to be understood that this invention encompasses both racemic and optically active forms of the physiologically active cyclopenta[g]quinazolines, it being a matter of common general knowledge how such optically active forms may be obtained by stereospecific synthesis or by separation of a mixture of isomeric compounds. It will be appreciated that one isomer may be of more interest than another due to the nature of the activity which it exhibits or due to superior physical properties, for example aqueous solubility.

It is also to be understood that a cyclopenta[g]quinazoline of the formula (I) may exhibit the phenomenon of tautomerism and that the formulae shown in this specification represent only one of the possible tautomeric forms. Moreover, it will be appreciated that when, for example, $Y_4$ or $Y_6$ is a tetrazol-5-yl group, that group may be in the form of a 1H-tetrazol-5-yl group or a 2H-tetrazol-5-yl group. It is to be understood therefore that the invention is not limited merely to any one tautomeric form which is illustrated.

It is also to be understood that certain cyclopenta[g] quinazolines of the formula (I) can exist in solvated as well as unsolvated forms such as, for example, hydrated forms.

A suitable value for $R^0$, $R^1$ or $R^2$ when it is $C_{1-4}$alkyl, or for a $C_{1-4}$ alkyl substituent which may be present on $Ar^1$ or $Ar_3$ or on a phenyl group-containing group $Y^4$ or $Y^6$ present in $R^3$, or for a group R present in $R^3$ when it is $C_{1-4}$ alkyl, is, for example, methyl, ethyl, propyl or isopropyl.

A suitable value for a $C_{1-4}$ alkoxy substituent which may be present on $Ar^1$ or $Ar^3$ or on a phenyl-containing group $Y^4$ or $Y^6$ is, for example, methoxy, ethoxy, propoxy, isopropoxy or butoxy.

A suitable value for a halogeno substituent which may be present on $Ar^1$ or $Ar^3$ or on a phenyl-containing group $Y^4$ or $Y^6$ is, for example, fluoro, chloro or bromo.

A suitable value for $R^0$, $R^1$ and $R^2$ when it is $C_{3-4}$ alkenyl or for a group R present in $R^3$ when it is alkenyl, is, for example, prop-2-enyl, but-2-enyl, but-3-enyl or 2-methylprop-2-enyl; and when it is $C_{3-4}$ alkynyl is, for example, prop-2-ynyl or but-3-ynyl.

A suitable value for $R^0$, $R^1$ and $R^2$ when it is $C_{2-4}$ hydroxyalkyl is, for example, 2-hydroxyethyl or 3-hydroxypropyl; when it is $C_{2-4}$ halogenoalkyl is, for example, 2-fluoroethyl, 2-chloroethyl, 2-bromoethyl, 3-fluoropropyl, 3-chloropropyl or 3-bromopropyl; and when it is $C^{1-4}$ cyanoalkyl is, for example, cyanomethyl, 2-cyanoethyl or 3-cyanopropyl.

When $R^0$ and $R^1$ together with the intermediate N form a five- or six-membered heterocyclic ring, this may bear substituents, but the ring is preferably an unsubstituted saturated ring such as pyrrolidine or piperidine.

A suitable value for $Ar^1$ or $Ar^3$ when it is phenylene is, for example, 1,3- or 1,4-phenylene, especially 1,4-phenylene.

A suitable value for $Ar^1$ or $Ar^3$ when it is thiophenediyl is, for example, thiophene-2,4-diyl or thiophene-2,5-diyl; when it is thiazolediyl is, for example thiazole-2,4-diyl or thiazole-2,5-diyl; when it is pyridinediyl is, for example, pyridine-2,4-diyl, pyridine2,5-diyl, pyridine-2,6diyl or pyridine-3,5-diyl; and when it is pyrimidinediyl is, for example, pyrimidine-2,4-diyl, pyrimidine2,5-diyl or pyrimidine-4,6-diyl.

As indicated, $Ar^1$ and a phenylene group $Ar^3$ may carry one or two substituents. A preferred level of substitution in $Ar^1$, where substitution is present, is either two substituents or especially one substituent; and the one or two substituents may conveniently be at positions adjacent to the atom bonded to the group —CONHCH($CO_2$H)—$R^3$, halogeno substituents such as fluoro being preferred. A preferred level of substitution on a phenylene group $Ar^3$, where substitution is present, is one substituent.

A preferred value for $Y^4$ or $y^6$ is tetrazol-5-yl or especially carboxy.

A suitable value for $A^5$ is, for example, methylene, ethylene, trimethylene, tetramethylene, pentamethylene or hexamethylene and a suitable value for R is as described hereinbefore. A suitable value for $Y^4$ when it is N—($C_{1-4}$ alkylsulfonyl)-carbamoyl is, for example, N-methylsulfonylcarbamoyl, N-ethylsulfonylcarbamoyl or N-propylsulfonylcarbamoyl.

A suitable value for $Y^5$ when it is the residue of a naturally occurring amino acid is alanine ($Y_5$=$CH_3$), arginine ($Y^5$= $(CH_2)_3NHC(NH_2)$=NH), aspartic acid ($Y^5$=$CH_2CO_2H$), cysteine ($Y^5$=$CH_2SH$), isoleucine ($Y^5$=$CH(CH_3)CH_2CH_3$), leucine ($y^5$=$CH_2CH(CH_3)CH_3$), ornithine $Y^5$=$(CH_2)_3NH_2$), phenylalanine ($Y^5$=$CH_2C_6H_5$), serine ($Y^5$=$CH_2OH$), valine ($Y^5$=$CH(CH_3)_2$), and especially glutamic acid ($Y^5$=$CH_2CH_2CO_2H$). When $Y^5$ is a group of the formula —$A^4CO_2$—H, a suitable value for $A^4$ is trimethylene, pentamethylene or hexamethylene, $A^4$ preferably being a $C_{3-6}$ alkylene group with especially suitable values for $Y^5$ being —$(CH_2)_nCO_2H$ where n is 3, 4 or 5.

A suitable value for $A^6$ in a group $Y^5$ of the formula -$A^6Ar^3$-$A^7$-$Y^6$ when it is a $C_{1-2}$ alkylene group is, for example methylene or ethylene, and for $A^7$ when it is a $C_{1-3}$ alkylene group is, for example, methylene, ethylene or trimethylene. A suitable value for $A^7$ when it is a $C_{2-3}$ alkenylene group is, for example, vinylene or especially propenylene (—$CH_2CH$=CH— or —CH=CH—$CH_2$). Suitable values for $Ar_3$ include those which have been discussed hereinbefore, such as thiophenediyl or most especially phenylene, or additionally tetrazole-1,5-diyl or tetrazole-2,5-diyl. A suitable value for $Y^6$ in such a group $Y^5$ when it is N—($C_{1-4}$ alkylsulfonyl)carbamoyl is, for example, N-methylsulfonylcarbamoyl, N-ethylsulfonylcarbamoyl or N-propylsulfonylcarbamoyl.

A suitable pharmaceutically-acceptable salt form of a cyclopenta[g]-quinazoline of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra (2-hydroxyethyl)ammonium, salt.

A suitable pharmaceutically-acceptable ester form of a cyclopenta[g]-quinazoline of the invention is, for example, an ester with an aliphatic alcohol of up to 6 carbon atoms, for example a methyl, ethyl or tert-butyl ester.

It is to be understood that $R^3$ may contain several carboxy groups in addition to the carboxy group in the grouping —ONHCH($CO_2$H)— When, for example, two carboxy groups are present in the cyclopenta[g]quinazoline, a salt or ester may be mono-acid-mono-salt or -ester, di-salt or di-ester and when, for example, three carboxy groups are present a salt or ester may be mono-acid-di-salt or -ester, di-acid-mono-salt or -ester or even tri-salt or -ester.

Particularly preferred values for the various symbols $R^0$, $R^1$, $R^2$ and $Ar^1$ individually are as expressed for the preferred cyclopenta[g]quinazolines described hereinafter.

A preferred cyclopenta[g]quinazoline of the invention has the formula (I) wherein $R^0$ and $R^1$ are each independently hydrogen or $C_{1-4}$ alkyl, especially methyl;

$R^2$ is ethyl, propyl, prop-2-enyl, prop-2-ynyl, 2-hydroxyethyl, 2-fluoroethyl, 2-bromoethyl or 2-cyanoethyl;

$Ar^1$ is 1,4-phenylene which may optionally bear one or two substituents selected from the group consisting of chloro and especially fluoro, thiophene-2,5-diyl, thiazole-2,5-diyl or pyridine-2,5-diyl;

$A^5$ is an ethylene group; and $Y^5$ is the residue of a naturally occurring amino acid $NH_2CH(CO_2H)Y^5$.

A preferred value for p is 1.

A further preferred cyclopenta[g]quinazoline of the invention has the formula (I) wherein A is hydrogen or a group $OR^0$ in which $R^0$ is hydrogen or methyl;

$R^2$ is ethyl or prop-2-ynyl;

$Ar^1$ is 1,4-phenylene or 1,4-phenylene having a 2-fluoro substituent as in 2,6-difluoro-1,4-phenylene or especially 2-fluoro-1,4-phenylene or is pyridine 2,5-diyl; and $A^5$ and $Y^5$ are just as described above.

An especially preferred cyclopenta[g]quinazoline of the invention has the formula (I) wherein A is hydrogen or a group $OR^0$ in which $R^0$ is hydrogen or methyl;

wherein $R^2$ is ethyl or preferably prop-2-ynyl;

$Ar^1$ is 1,4-phenylene or 2-fluoro-1,4-phenylene; and $R^3$ is the residue of an acid $NH_2CH(COOH)R^3$ which comprises L-Glu-γ-D-Glu, i.e. N-L-γ-glutamyl-D-glutamic acid, or L-Glu-γ-L-Glu, i.e. N-L-γ-glutamyl-L-glutamic acid wherein $R^3$ is of formula:

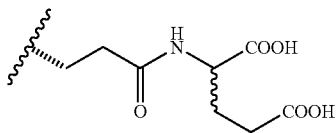

$R^3$ is the corresponding N-methyl derivative of formula:

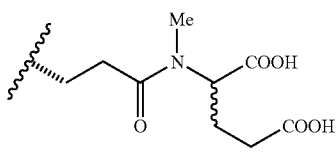

or $R^3$ is the corresponding tetrazol-5-yl derivative of formula:

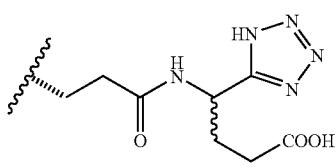

Other quinazolines of the invention of particular interest have the values of $R^0$, $R^1$, $R^2$, and $Ar^1$ and Ar in combination as indicated above but with $R^3$ having any value as indicated hereinbefore. However, specific particularly preferred cyclopenta-[g]quinazolines of the invention are:

N-{-{4-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid;

N-{N-{2-fluoro-4-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid;

(4R)-4-{N{N-{4-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl}-amino}-4-(tetrazol-5-yl)butyric acid;

N-{N-{4-[N-((6RS)-2-hydroxymethyl4-oxo-3,4,7,8-tetrahydro-6H-cyclopenta[g]quinazolin-6-yl)-N-(prop-2-ynyl) amino]benzoyl}-L-γ-glutamyl}-D-glutamic acid;

N-methyl-N-{N-{4-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl}-L-glutamic acid; and N-{N-{4-[N-((6RS)-2-hydroxymethyl-4-oxo-3,4,7,8-tetrahydro-6H-cyclopenta[g]quinazolin-6-yl)-N-(prop-2-ynyl) amino]benzoyl}-L-γ-glutamyl}-N-methyl-L-glutamic acid;

or a pharmaceutically acceptable salt or ester thereof.

Although the compounds of the present invention can exist as a mixture of stereoisomers it is preferred that they are resolved into one optically active isomeric form. Such a requirement complicates the synthesis of the compounds and it is preferred therefore that they contain as few asymmetric carbon atoms as possible consistent with achieving the desired activity.

As indicated previously, however, the cyclopenta[g] quinazolines of the present invention contain at least two asymmetric carbon atoms. Of these, that at the 6 position of the ring system preferably has the 6S orientation rather than the 6R orientation, whilst the alpha carbon atom of the group —CONHCH(CO₂H)— preferably has the L rather than the D configuration. The preferred compounds (I) described hereinbefore thus preferably have such a configuration at these two asymmetric carbon atoms or less preferably are a racemic mixture in which one or both of these asymmetric carbon atoms is unresolved.

The asymmetric carbon atom of a residue -$A^5$-CON(R)CH($Y^4$)$Y^5$ may be of the L- or D-configuration but the amide bond will be stabilised in vivo when it is of the D-configuration as it will also be when R is other than hydrogen. When $Y^5$ is the residue of a naturally occurring amino acid, however, the amino acid intermediate for the synthesis of the cyclopenta[g]quinazoline will of course be more readily available when this asymmetric carbon atom is of the L-configuration.

A cyclopenta[g]quinazoline of the invention may be prepared by any process known to be applicable to the preparation of chemically-related compounds.

The anti-cancer activity of the cyclopenta[g]quinazolines of the present invention may be assessed, for example, using one or more of the procedures set out below:

(a) An in vitro assay which determines the ability of a test compound to inhibit the enzyme thymidylate synthase. Thymidylate synthase may be obtained in partially purified form from L1210 mouse leukaemia cells and utilised in the assay using the procedures described by Jackman et al. (*Cancer Res.*, 1986, 46, 2810) and Sikora et al. (*Biochem. Pharmacol.*, 1988, 37, 4047), (b) An assay which determines the ability of a test compound to bind to the α-FR relative to that of folic acid, using mouse L1210FBP cells (α-FR expression) in the procedure described by Westerhof et al. (*Cancer Res.*, 1991, 51, 5507-5513);

(c) An assay which determines the ability of a test compound to inhibit the growth of human tumour cell lines expressing the α-FR (A431-FBP vulvular carcinoma transfected with the α-FR; KB nasopharengeal carcinoma);

(d) An assay which determines the ability of a test compound to inhibit the growth of human tumour cell lines not expressing the α-FR (A431 neo-transfected);

(e) An assay confirming or demonstrating that compound-induced growth inhibition is largely attributable to α-FR mediated uptake into KB or A431-FBP cells. This involves the co-addition of an excess of folic acid (1 µM) to compete with the compounds for FR but not RFC binding.

Although the pharmacological properties of the cyclopenta[g]quinazolines of the invention depend on their detailed structure, in general the cyclopenta[g]quinazolines of the invention possess activity in one or more of the above tests (a) to (d) as indicated below:

| | |
|---|---|
| Test (a) | $IC_{50}$ in the range, for example, 0.0001-1 µM; |
| Test (b) | Inverse relative affinity in the range, for example, 0.05-5 (values greater than 1 implies binding is greater than that of folic acid and values less that 1 implies binding weaker than that of folic acid); |
| Test (c) | $IC_{50}$ in the range, for example, 0.001-10 µM; |
| Test (d) | $IC_{50}$ in the range, for example, 0.01-100 µM; |
| Test (e) | $IC_{50}$ at least 10-fold higher than that seen in test (b) for the same cell line. |

A cyclopenta[g]quinazoline of the present invention may itself be active or it may be a pro-drug which is converted in vivo to an active compound. A cyclopenta[g]quinazoline of the invention may be administered to a warm-blooded animal, including a human, in the form of a pharmaceutical composition which comprises the cyclopenta[g]quinazoline in association with a pharmaceutically-acceptable diluent or carrier.

The composition may be in a form suitable for oral use, for example a tablet, capsule, aqueous or oily solution, suspension or emulsion; a form suitable for topical use, for example a cream, ointment, gel or aqueous or oily solution or suspension: a form suitable for nasal use, for example a snuff, nasal spray or nasal drops; a form suitable for vaginal or rectal use, for example a suppository, a form suitable for administration by inhalation, for example as a finely divided powder such as a dry powder, a microcrystalline form or a liquid aerosol; a form suitable for sub-lingual or buccal use, for example a tablet or capsule; or a form suitable for parenteral use (including intravenous, subcutaneous, intramuscular, intravascular or infusion use), for example a sterile aqueous or oily solution, emulsion or suspension. In general the above compositions may be prepared in a conventional manner using convention excipients.

The composition may contain, in addition to the cyclopenta[g]quinazoline of the invention, one or more other anti-cancer substances selected from, for example, other antimetabolites, DNA interacting agents, signal transduction inhibitors or other inhibitors of deregulated pathways in tumours.

The cyclopenta[g]quinazoline will normally be administered to a warm-blooded animal at a dose within a range of 50-25000, particularly 50-5000, mg per square meter body area of the animal, i.e. approximately 1500, particularly 1-100, mg/kg. Where desired, however, dosages outside this range may be employed and, in particular, where the preferred mode of administration involving subcutaneous infusion is used then the does range may be increased to 1-1000 mg/kg. Preferably a daily dose in the range 10-250 mg/kg is employed, particularly 30-150 mg/kg. However, the daily dose will necessarily be varied depending upon the host treated, the particular route of administration and the severity of the illness being treated. Accordingly, the optimum dosage may be determined by the practitioner who is treating any particular patient.

Accordingly the present invention also includes a method for aiding regression and palliation of cancer in a patient, particularly a warm-blooded animal such as a human, in need of such treatment, which comprises administering to said patient an effective amount of a cyclopenta[g]quinazoline as defined hereinbefore.

Cyclopenta[g]quinazolines of the present invention are of interest for a wide range of anti-tumour activities against solid tumours, but particularly the treatment of ovarian cancer.

In view of the activity shown by antimetabolites such as aminopterin and methotrexate, which is discussed hereinbefore, the cyclopenta[g]quinazolines of the present invention are also of interest for use in the treatment of other conditions, for example allergic conditions such as psoriasis and inflammatory diseases such as rheumatoid arthritis. In using a cyclopenta[g]quinazoline of the invention for such a purpose the compound will normally be administered at a dose within the range 5-25000, particularly 5-500, mg per square meter body area of the animal, i.e. approximately 0.1-500, particularly 0.1-10, mg/kg. Where desired, however, dosages outside this range may be employed. In general, for the treatment of an allergic condition such as psoriasis, topical administration of a cyclopenta[g]quinazoline of the invention is preferred. Thus, for example, for topical administration a daily dose in the range, for example, of 0.1 to 10 mg/kg may be used.

Compositions containing the quinazolines may be formulated in unit dosage form, i.e. in the form of discrete portions each comprising a unit dose, or a multiple or sub-multiple of a unit dose, for example as a tablet or capsule. Such a unit dosage form may, for example, contain an amount of the cyclopenta[g]quinazoline in the range of 1-250 or 1-500 mg.

The invention is illustrated by the following Examples.

EXAMPLE 1

Synthesis of CB300945 (2-$CH_2OH$ Derivative of CB300638)

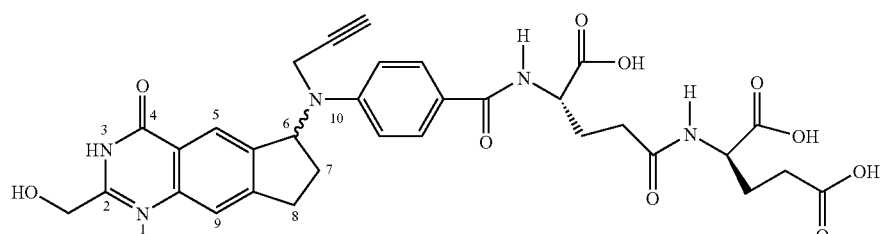

CB300945

2-Hydroxymethyl-3,4,7,8-tetrahydro-6H-cyclopenta[g]quinazolin-4-one

A solution of caesium acetate (14.4 g, 75.2 mmol) in dry DMF (40 ml) was heated to 60° C. under argon for 30 min. The mixture was cooled to 40° C. and a suspension of 2-chloromethyl-3,4,7,8-tetrahydro-6H-cyclopenta[g]quinazolin-4one (L. Skelton, V. Bavetsias, A. Jackman, WO 00/050417-A1; 2.2 g, 9.4 mmol) in dry DMF (60 ml) was added via a cannula. The mixture was heated to 80° C. under argon for 16 h. The mixture was cooled to room temperature and the solvent was removed in vacuo. The residue was suspended in water (50 ml) and MeOH (20 ml). The pH was adjusted to 12.5 with 1 M sodium hydroxide solution and the brown suspension was stirred for 2 h at room temperature. The insoluble brown solid was removed by filtration and the resulting solution was acidified to pH 5 with 1M hydrochloric acid. The precipitate was collected by filtration, washed with acidified water and dried in vacuo over $P_2O_5$ to yield the product as a pale yellow solid (1.17 g, 58%); m.p. 205-210° C.; $^1$H NMR (DMSO-$d_6$) δ 2.07 (quin, J=7.4 Hz, 2H, 7-H), 2.98 (q, J=6.95 Hz, 4H, 6-H and 8-H), 4.38 (s, 2H, 2-$CH_2$), 7.46 (s, 1H, 9-H), 7.92 (s, 1H, 5-H); MS (FAB-m/z): Found 217 [(M+H)$^+$, 100%]; HRMS: measured 217.0977; calculated for $C_{12}H_{13}N_2O_2$ (M+H)$^+$: 217.0977; Found C, 64.01; H, 5.23; N, 12.34. $C_{12}H_{13}N_2O_2·½H_2O$ requires C, 63.93; H, 5.77; N, 12.43%.

2-(2,2-Dimethylpropionyloxymethlyl)-3,4,7,8-tetrahydro-6H-cyclopenta-[g]quinazolin-4-one 2-Hydroxymethyl-3,4,7,8-tetrahydro-6H-cyclopenta[g]quinazolin-4-one (1.0 g, 4.6 mmol), triethylamine (0.77 ml, 5.6 mmol), DMAP (50 mg, 0.4 mmol) and anhydrous $CH_2Cl_2$ (50 ml) were mixed in a flask under argon. Pivalic anhydride (1.2 ml, 6.0 mmol) was added dropwise and the suspension stirred at room temperature under argon for 5 h. The solvent was removed in vacuo and the residue partitioned between EtOAc (100 ml) and saturated aqueous $NaHCO_3$ (100 ml). The organic extract was washed with saturated aqueous $NaHCO_3$ (70 ml), water (70 ml), brine (70 ml), dried ($Na_2SO_4$) and the solvent removed in vacuo. The residue was triturated with hexane (60 ml) and the product collected by filtration as a yellow solid (1.21 g, 87%); m.p. 185-190° C.; $^1$H-NMR (DMSO-$d_6$) δ 1.22 (s, 9H, CMe$_3$), 2.07 (quin, J=7.4 Hz, 2H, 7-H), 2.98 (q, J=5.72 Hz, 4H, 6-H and 8-H), 4.94 (s, 2H, 2-$CH_2$), 7.42 (s, 1H, 9-H), 7.92 (s, 1H, 5-H), 12.20 (br, 1H, NH); MS (FAB, m/z): Found 301 [(M+H)$^+$, 100%]; HRMS: measured 301.1539; calculated for $C_{17}H_{21}N_2O_3$ (M+H)$^+$: 301.1552; Found C, 67.65; H, 6.54, N, 9.54, $C_{17}H_{20}N_2O_3$ requires C, 67.98; H, 6.71; N, 9.33%.

2-(2,2-Dimethylpropionyloxymethyl)-3,4,7,8-tetrahydro-6H-cyclopenta[g]quinazolin-4,6-dione and 2-(2,2-Dimethylpropionyloxymethyl)-3,4,7,8-tetrahydro-6H-cyclopenta[g]quinazolin-4,8dione To a stirred solution of $(Ph_3SiO)_2CrO_2$ (L. M. Baker and W. L. Carrick, J. Org. Chem. 1970, 35, 774) (10.6 mg, 0.017 mmol) in $CH_2Cl_2$ (5 ml) was added sequentially aqueous 70% tert-butyl hydroperoxide (0.18 ml, 1.3 mmol) and 2-(2,2-dimethylpropionyloxymethyl)-3,4,7,8-tetrahydro-6H-cyclopenta[g]quinazolin-4-one (0.1 g, 0.33 mmol). The mixture was stirred at room temperature with protection from the light for 24 h. The solvents were removed in vacuo and the residue purified by column chromatography (20 g of silica gel) eluting with a gradient of 10-30% EtOAc in $CHCl_3$ to yield 2-(2,2-dimethylpropionyloxymethyl)-3,4,7,8-tetrahydro-6H-cyclopenta[g]quinazolin-4,6-dione as a white solid (47 mg, 45%); m.p. 185-190C; $^1$H-NMR (DMSO-$d_6$) δ 1.23 (s, 9H, CMe$_3$), 2.72 (m, 2H, 7-H), 3.25 (m, 2H, 8-H), 5.00 (s, 2H, 2-$CH_2$), 7.70 (s, 1H, 9-H), 8.29 (s, 1H, 5-H), 12.20 (br, 1H, NH); MS (FAB, m/z): Found 315 [(M+H)$^+$, 100%], 337 [(M+Na)$^+$, 75%]; HRMS; measured 315.1360; calculated for $C_{17}H_{19}N_2O_4$ (M+H)$^+$: 315.1345; Found C, 64.18; H, 5.72; N, 8.81. $C_{17}H_{18}N_2O_4·0.2H_2O$ requires C, 64.23; H, 5.79; N, 8.82%.

2-(2,2-Dimethylpropionyloxymethyl3,4,7,8-tetrahydro-6H-cyclopenta[g]-quinazolin-4,8-dione; $^1$H-NMR (DMSO-$d_6$) δ 1.23 (s, 9H, CMe$_3$), 2.76 (m, 2H, 7-H), 3.26 (m, 2H, 8-H), 4.98 (s, 2H, 2-$CH_2$), 7.72 (s, 1H, 9-H), 8.29 (s, 1H, 5-H), 12.3 (br, 1H, NH).

tert-Butyl 4-[N-((6RS)-2-(2,2-dimethylpropionyloxymethyl)-4-oxo-3,4,7,8-tetrahydro-6H-cyclopenta[g]quinazolin-6-yl)amino]benzoate A suspension of 2-(2,2dimethylpropionyloxymethyl)-3,4,7,8-tetrahydro-6H-cyclopenta[g]quinazolin-4,6-dione (0.47 g, 1.50 mmol) in anhydrous methanol (33 ml) and anhydrous $CH_2Cl_2$ (5 ml) was treated with tert-butyl 4-aminobenzoate (0.34 g, 1.78 mmol) followed by decaborane (0.07g, 0.58 mmol) and the mixture stirred at room temperature under argon for 18 h. The solvent was removed in vacuo and the residue purified by column chromatography (50 g of silica gel) eluting with 30% ethyl acetate in $CH_2Cl_2$ to yield the desired product as a white solid (0.43 g, 58%); m.p. 231° C., $^1$H-NMR (CDCl$_3$) δ 1.26 (s, 9H, CMe$_3$), 1.58 (s, 9H, CO$_2$CMe$_3$), 2.00 (m, 1H, 7-H), 2.72 (m, 1H, 7-H), 3.08 (m, 2H, 8-H), 5.10 (s, 2H, 2-$CH_2$), 5.15 (m, 1H, 6-H), 6.67 (d, J=8.8 Hz, 2H, 3'-H, 5'-H), 7.58 (s, 1H, 9-H), 7.87 (d, J=8.8 Hz, 2H, 2'-H, 6'-H), 8.24 (s, 1H, 5-H); MS (FAB, m/z): Found 491 [(M+H)$^+$, 25%], 514 [(M+Na)$^+$, 100%]; Found C, 68.37; H, 6.86; N, 8.35. $C_{28}H_{33}N_3O_5$ requires C, 68.41; H, 6.77; N, 8.55%.

tert-Butyl 4-[N((6RS)-2-(2,2-dimethylpropionyloxymethyl)4-oxo-3,4,7,8-tetrahydro-6H-cyclopenta[g]quinazolin-6-yl)-N-(prop-2-ynyl)amino]benzoate A suspension of (propargyl)Co$_2$(CO)$_6$$^+$BF$_4$$^-$(213 mg, 0.52 mmol) in anhydrous $CH_2Cl_2$ (25 ml) was treated with tert-butyl 4-[N-((6RS)-2-(2,2-dimethylpropionyloxymethyl)-4-oxo-3,4,7,8-tetrahydro-6H-cyclopenta[g]quinazolin6-yl)-amino]benzoate (200 mg, 0.41 mmol) and the red solution stirred at room temperature under argon for 15 minutes. Diisopropylethylamine (0.15 ml. 0.86 mmol) was added and the mixture stirred at room temperature under argon for 1 h. The mixture was partitioned between ethyl acetate (30 ml) and brine (30 ml). The organic extract was dried (Na$_2$SO$_4$) and the solvent removed in vacuo. The residue was purified by column chromatography (20 g of silica gel) eluting with a gradient of 0-10% ethyl acetate in $CH_2Cl_2$ to yield the complex as a red oil (191 mg, 58%); $^1$H-NMR (CDCl$_3$) δ 1.26 (s, 9H, CMe$_3$), 1.59 (s, 9H, CO$_2$CMe$_3$), 2.31 (m, 1H, 7-H), 2.62 (m, 1H, 7-H), 3.13 (m, 2H, 8-H), 4.57 (AB system, J=16.9 Hz, 2H, propargyl CH$_2$), 5,09 (s, 2H, 2-$CH_2$), 5.63 (t, J=8.3, 1H, 6-H), 5.98 (s, 1H, propargyl CH), 6.91 (d, J=8.9 Hz, 2H, 3'-H, 5'-H), 7.61 (s, 1H, 9-H), 7.90 (d, J=8.9 Hz, 2H, 2'-H, 6'-H), 8.14 (s, 1H, 5-H), 10.25 (br s, 1H).

A solution of this complex (186 mg, 0.23 mmol) in ethanol (30 ml) was treated with Fe(NO$_3$)$_3$·9H$_2$O (1.1 g) and the solution stirred at room temperature for 2 h. The solution was partitioned between ethyl acetate (30 ml) and water (30 ml).

The organic extract was washed with brine (30 ml), dried (Na$_2$SO$_4$) and the solvent removed in vacuo. The residue was purified by column chromatography (20 g of silica gel) eluting with 10% ethyl acetate in CH$_2$Cl$_2$ to yield the desired product as a white solid (94 mg, 78%); m.p. 134° C.; $^1$H-NMR (CDCl$_3$) δ 1.32 (s, 9H, CMe$_3$), 1.61 (s, 9H, CO$_2$CMe$_3$), 2.23 (s, 1H, propargyl CH), 2.38 (m, 1H, 7-H), 2.62 (m, 1H, 7-H), 3.07 (m, 1H, 8-H), 3.25 (m, 1H, 8-H), 3.94 (AB system, J=18.6 Hz, 2H propargyl CH$_2$), 5.12 (s, 2H, 2-CH2), 5.68 (t, J=8.2 Hz, 1H, 6-H), 6.99 (d, J=9.1 Hz, 2H, 3'-H, 5'-H), 7.63 (s, 1H, 9-H), 7.95 (d, J=9.0 Hz) 2H, 2'-H, 6'-H), 8.16 (s, 1H, 5-H), 9.55 (br s, 1H), MS (ESI, m/z) 552 {(M+Na)$^+$, 100%}, 530 {(M+H$^+$, 20%}; Found C, 70.14; H, 6.80; N, 7.73. C$_{31}$H$_{35}$N$_3$O$_5$ requires C, 70.30; H, 6.66; N, 7.93%.

4-[N-((6RS)-2-(2,2-Dimethylpropionyloxymethyl)-4-oxo-3,4,7,8-tetrahydro-6H-cyclopenta[g]quinazolin-6-yl)-N-(prop-2-ynyl)amino]benzoic acid A solution of tert-butyl 4-[N-((6RS)-2-(2,2dimethylpropionyloxymethyl)-4-oxo-3,4,7,8-tetrahydro-6H-cyclopenta[g]quinazolin-6-yl)-N-(prop2-ynyl)amino]-benzoate (80 mg, 0.15 mmol) in trifluoroacetic acid (5 ml) was stirred at room temperature with protection from the light for 1.5 h. The solvent was removed in vacuo and the residue triturated with 1:1 diethyl ether and hexane to yield the desired product as a white solid (81 mg, TFA salt); m.p. 133° C., $^1$H-NMR (DMSO-d6) δ 1.23 (s, 9H, CO$_2$CMc$_3$), 2.22 (m, 1H, 7-H), 2.50 (m, 1H, 7-H), 3.03 (m, 2H, 8-H), 3.14 (s, 1H, propargyl CH), 3.97 (AB system, J=18.8 Hz, 2H, propargyl CH$_2$), 4.95 (s, 2H, 2-CH$_2$), 5.79 (t, J=8.6 Hz, 1H, 6-H), 7.03 (d, J=9.0 Hz, 2H, 3'-H, 5'-H), 7.51 (s, 1H, 9-H), 7.81 (d, J=6.6 Hz, 2H, 2'-H, 6'-H), 7.83 (s, 1H, 5-H).

Tri-tert-butyl N-{N-{4-[N-((6RS)2-(2,2-dimethylpropionyloxymethyl)-4-oxo-3,4,7,8-tetrahydro-6H-cyclopenta[g]quinazolin-6-yl)-N-(prop-2-ynyl)-amino]benzoyl}-L-γ-glutamyl}-D-glutamate A solution of 4-[N-((6RS)-2-(2,2-dimethylpropionyloxymethyl)-4oxo-3,4,7,8-tetrahydro-6H-cyclopenta[g]quinazolin-6-yl)-N-(prop-2-ynyl)amino]benzoic acid (80 mg, 0.15 mmol) in anhydrous dimethylformamide (7 ml) was treated with tri-tert butyl-L-γ-glutamyl-D-glutamate (150 mg, 0.33 mmol), diethyl cyanophosphonate (0.06 ml, 0.40 mmol) and triethylamine (0.06 ml, 0.40 mmol). The solution was stirred at room temperature under argon with protection from the light for 2.5 h. The solution was partitioned between ethyl acetate (25 ml) and water (25 ml). The aqueous layer was extracted with ethyl acetate (2×20 ml). The combined organic extracts were washed with 10% aqueous citric acid (2×30 ml), saturated aqueous NaHCO$_3$ (30 ml), dilute brine (30 ml), dried (Na$_2$SO$_4$) and the solvent removed in vacuo. The residue was purified by column chromatography (30 g of silica gel) eluting with 40% ethyl acetate in CH$_2$Cl$_2$ to yield the desired product as a white solid (94 mg, 62%); m.p. 109° C.; $^1$H-NMR (CDCl$_3$) δ 1.29 (s, 9H, —COCMe$_3$), 1.43 (s, 9H, COOCMe$_3$), 1.47 (s, 9H, COOCMe$_3$), 1.48 (s, 9H, COOCMe$_3$), 1.60-2.10 (m, 5H, 2×glu β-CH$_2$, 7-CH), 2.21 (s, 1H, propargyl CH), 2.22-2.50 (m, 4H, 2×glu γ-CH$_2$), 2.59 (m, 1H, 7-H), 3.08 (n, 1H, 8-H), 3.20 (m, 1H, 8-H), 3.92 (AB system, J=19.0 Hz, 2H, propargyl CH$_2$), 4.48, 4.76 (2×m, 2H, 2×glu α-CH), 5.12 (s, 2H, 2-CH$_2$), 5.64 (t, J=8.1 Hz, 1H, 6-H), 6.99 (d, J=8.8 Hz, 2H, 3'-H, 5'-H), 7.07 (m, 2H, 2×CONH), 7.64 (s, 1H, 9-H), 7.80 (d, J=8.8 Hz, 2H, 2'-H, 6'-H), 8.13 (s, 1H, 5-H); MS (ESI, m/z) 922 {(M+Na)$^+$, 100%}, 900 {(M+H)$^+$, 40%}; Found C, 64.85; H, 7.23; N, 7.33. C$_{49}$H$_{65}$N$_5$O$_{11}$.0.5H$_2$O requires C, 64.76;H, 7.27, N, 7.71%.

N-{N-{4[N-((6RS-2-Hydroxymethyl4-oxo-3,4,7,8-tetrahydro-6H-cyclopenta[g]quinazolin-6-yl)-N-(prop-2-ynyl)amino]benzoyl}-L-γ-glutamyl}-D-glutamic Acid Tri-tert-butyl N-{N-{4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]-benzoyl}-L-γ-glutamyl}-D-glutamate (80 mg, 0.09 mmol) was dissolved in trifluoroacetic acid (5 ml) and stirred at room temperature with protection from the light for 1 h. The solvent was removed in vacuo and the residue dissolved in methanol (3 ml) and water (3 ml). The pH of the solution was adjusted to pH 12 with 1M sodium hydroxide solution and stirred at room temperature for 6 h. The solution was acidified to pH 4 with 1M hydrochloric acid and cooled to 0° C. The precipitate was collected by filtration and dried under vacuum over P$_2$O$_5$ to yield the desired product as a pale brown solid (27 mg, 47%); m.p. 172° C.; $^1$H-NMR (DMSO-d$_6$) δ 1.60-2.10 (m, 5H, 2×glu β-CH$_2$, 7-CH), 2.15-2.40 (m, 5H, 2×glu γ-CH$_2$, 7-H), 2.99 (m, 1H, 8-H), 3.12 (s, 1H, propargyl CH), 3.16 (m, 1H, 8-H), 3.98 (AB system, J=19.9 Hz, 2H, propargyl CH$_2$), 4.18, 4.30 (2×m, 2H, 2×glu α-CH), 4.36 (s, 2H, 2-CH$_2$), 5.58 (br s, 1H, —OH), 5.77 (t, J=7.9 Hz, 1H, 6-H), 7.01 (d, J=8.9 Hz, 2H, 3'-H, 5'-H), 7.54 (s, 1H, 9-H), 7.80 (d, J=8.5 Hz, 2H, 2'-H, 6'-M), 7.82 (s, 1H, 5-H), 8.15 (d, J=7.5 Hz, 1 H), 8.35 (d, J=7.2 Hz, 1 H) (2×CONH); MS (ESI, m/z) 670 {(M+Na)$^+$, 45%}, 648 {(M+H)$^+$, 100%}; HRMS: measured 648.2313; calculated for C$_{32}$H$_{35}$N$_5$O$_{10}$ (M+H)$^+$; 648.2306.

EXAMPLE 2

Synthesis of CB300947

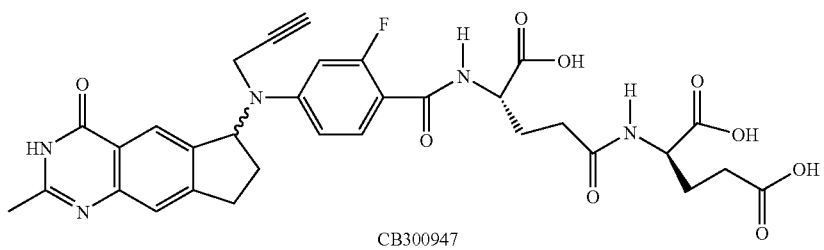

CB300947 ert-Butyl 4-[N-(5-acetamido-6-bromoindan-1-yl) amino]-2-fluorobenzoate

To a solution of 5-acetamido-6-bromoindan-1-one (0.370 g, 1.38 mmol) in anhydrous methanol (32 ml) was added tert-butyl 4-amino-2-fluorobenzoate (V. Bavetsias et al, *J Med. Chem.* 1996, 39, 73-85; 0.322 g, 1.52 mmol) followed by decaborane (0.030 g). The reaction mixture was stirred at room temperature for 11 hours then more decaborane (0.005 g) was added and stirring was continued for a longer 12 hours under argon. The solvent was removed in vacuo, and the residue was purified by column chromatography eluting with a gradient of ethyl acetate in hexane (30 to 40%). The desired compound was obtained as a white solid 0.455 g (71%) m.p.>70° C. (softens); $^1$H-NMR (250 MHz, CDCl$_3$, TMS) 1.57 (s, 9H, C(CH$_3$)$_3$), 2.24 (s, 3H, COCH$_3$), 1.98, 2.56 (2×m, 2H, indanyl 2-H), 2.94 (m, 2H, indanyl 3-H), 4.33 (d, J=7.90 Hz, 1H, N-H), 4.99 (q, J=7.06 Hz, 1H, indanyl 1-H), 6.37 (m, 2H, 3,5-H), 7.48, 8.25, 7.60 (3×s, each 1H, indanyl 4H, 7-H, CONH), 7.72 (t, J=8.75 Hz, 6-H); MS (ESI, m/z) 485, 487 {(M+Na)$^+$, bromine isotopic pattern}.

Tert-butyl 4-[N-(5-acetamido-6-cyanoindan-1-yl) amino]-2-fluorobenzoate

To a solution of tert-butyl 4-[N-(5-acetamido-6-bromoindan-1-yl)amino]-2-fluorobenzoate (0.420 g, 0.90 mmol) in NMP (10 ml) was added copper(I) cyanide (0.137 g, 1.53 mmol). The reaction mixture was placed in an oil-bath preheated to 145° C. and stirred at this temperature for 2 hours. The reaction mixture was allowed to cool to room temperature, then poured into a mixture of aqueous ammonia (d=0.88, 5 ml) and ice (~15 ml) and the resulting brown mixture was stirred at room temperature for ~5 min. The brown solid was collected by filtration washed with water, then suspended in dichloromethane (60 ml). The mixture was stirred at room temperature for 5 min, dried (Na$_2$SO$_4$), and concentrated in vacuo. Purification by column chromatography, on elution with 40% ethyl acetate in hexane, afforded a solid that was triturated with diethyl ether/hexane. The desired compound was obtained as a white solid: 0.202 g, (55%) m.p. 172-173° C.; $^1$H-NMR (250 MHz, CDCl$_3$, TMS) 1.57 (s(obscured by water peak), 9H, C(CH$_3$)$_3$), 2.27 (s, 3H, COCH$_3$), 1.96, 2.65 (2×m, 2H, indanyl 2-H), 3.00 (m, 2H, indanyl 3-H), 4.30 (d, J=8.40 Hz, 1H, N-H), 4.99 (q, J=7.80 Hz, 1H, indanyl 1-H), 6.38 (m, 2H, 3,5-H), 7.52, 8.33, 7.62 (3×s, each 1H, indanyl 4-H, 7-H, CONH), 7.74 (t, J=8.60 Hz, 1H, 6-H); MS (ESI, m/z) 432 {(M+Na)$^+$, 100%}; Found: C, 67.44; H, 5.88; N, 10.25; P, 4.63; C$_{23}$H$_{24}$FN$_3$O$_3$ requires C, 67.47; H, 5.91; N, 10.26%; F, 4.64%.

tert-Butyl 4-{N-[(6RS)-2-methyl-4-oxo-3,4,7,8-tetrahydro-6H-cyclopenta-[g]quinazolin-6yl]amino}-2-fluorobenzoate A mixture of tert-butyl 4-[N-(5-acetamido-6-cyanoindan-1-yl)amino]-$^2$-fluorobenzoate (0.182 g, 0.44 mmol), ethanol (2 ml), and water (0.4 ml) was cooled in an ice-bath, then 30% aqueous H$_2$O$_2$ solution (0.37 ml) was added followed by granulated sodium hydroxide pellets (0.030 g, 0.75 mmol). The reaction mixture was stirred at ~0° C. for 10 min, then it was placed in an oil bath preheated to 55° C. and stirred at this temperature for 30 min The reaction mixture was allowed to cool to room temperature, then the solvents were removed in vacuo and the residue was suspended in water (~15 ml). The pH of this mixture was adjusted to ~4 with 1N hydrochloric acid. The white precipitate was collected by filtration, washed with water, and dried in vacuo over P$_2$O$_5$. The desired compound was obtained as a white solid 0.155 g (85%), m.p. 150-152° C.; $^1$H-N (250 MHz, DMSO-d$_6$, TMS) 1.50 (s, 9H, C(C$_3$)$_3$), 2.32 (s, 3H, 2-CH$_3$), 1.83, 2.53 (2×m, 2H, 7-H), 3.00 (m, 2H, 8-H), 5.15 (q, J=7.40 Hz, 1H, 6-H), 6.57 (m, 2H, 3',5'-H), 7.16 (d, J=7.75 Hz, 1H, N$^{10}$—H), 7.44, 7.87 (2×s, each 1H, 5-H, 9-H), 7.59 (t, J=8.73 Hz, 6'-H), 12.11 (s, 1H, N$^3$-H), MS (ESI, m/z) 819 {(2M+H)$^+$, 100%}, 432 {(M+Na)$^+$, 10%}, 410 {M+H)$^+$, 15%}; Found: C, 66.81; H, 5.89, N, 10.11; F, 4.58; C$_{23}$H$_{24}$FN$_3$O$_3$·0.25H$_2$O requires C, 66.74; H, 5.96; N, 10.15%; F, 4.59%.

(Propargyl)Co$_2$(CO)$_6$$^+$BF$_4$$^-$

This was prepared as in Example 1 from the dicobalthexacarbonyl propargyl alcohol complex. It was used immediately in the next reaction without any further purification.

Tert-Butyl 4-{N-[(6RS)-2-methyl-4-oxo-3,4,7,8-tetrahydro-6H-cyclopenta-[g]quinazolin-6-yl]-N-(prop-2-ynyl)amino}-2-fluorobenzoate To a round-bottomed flask containing (propargyl)Co$_2$(CO)$_6$$^+$BF$_4$$^-$ (0.174 g, 0.43 mmol) was added anhydrous dichloromethane (dried by distillation over P$_2$O$_5$; 14 ml). The solution was stirred at room temperature for few minutes under argon, then tert-butyl 4-{N-[(6RS)-2-methyl-4-oxo-3,4,7,8-tetrahydro-6H-cyclopenta[g]-quinazolin-6-yl]amino}-2-fluorobenzoate (0.135 g, 0.33 mmol) was added. Stirring was continued at this temperature for 5 min then diisopropylethylamine (0.4 ml) was added and the reaction mixture was stirred at room temperature for 25 min under argon. The reaction mixture was partitioned between ethyl acetate (80 ml) and brine (40 ml). The organic layer was washed with 10% aqueous citric acid (30 ml), brine (40 ml), dried (Na$_2$SO$_4$), and concentrated in vacuo. Purification by column chromatography, on gradient elution with ethyl acetate in dichloromethane (25 to 50%), gave a red solid 0.140 g (58%); $^1$H-NMR (250 MHz, CDCl$_3$, TMS) 1.58 (s, 9H, C(CH$_3$)$_3$), 2.54 (s, 3H, 2-Mc), 2.32, 2.61 (m, each 1H, 7-H), 3.03, 3.23 (m, each 1H, 8-H), 4.55 (ABq, J=16.92 Hz, 2H, N$^{10}$—CH$_2$), 5.59 (t, J=8.30, 1H, 6-H), 6.00 (s, 1H, propargyl complex C—H), 6.59 (d, J=14.52 Hz, 1H, 3'-H), 6.69 (d, J=8.70 Hz, 1H, 5'-H), 7.58, 7.98 (s, each 1H, 5-H, 9-H), 7.79 (d, J=8.82 Hz, 6'-H), 10.96 (s, 1H, N$^3$-H). To a solution of this complex (0.100 g, 0.136 mmol) in ethanol (15 ml) was added Fe(NO$_3$)$_3$·9H$_2$O (~2 g). The clear solution was stirred at room temperature for 5 min then a second portion of Fe(NO$_3$)$_3$·9H$_2$O (~1.0 g) was added. The reaction mixture was stirred at room temperature for a longer 25 min then a final portion of Fe(NO$_3$)$_3$·9H$_2$O (~1.2 g) was added. Stirring was continued at room temperature for an extra 35 min, then the reaction mixture was partitioned between ethyl acetate (70 ml) and water (30 ml). The organic layer was washed with brine (2×30 ml), dried (Na$_2$SO$_4$), and concentrated in vacuo to leave a crispy solid. Purification by column chromatography, on elution with 5% methanol in chloroform, afforded a white solid; 0.040 g (67%), m.p 248-250 ° C., $^1$H-NMR (250 MHz, DMSO-d$_6$, TMS) 1.50 (s, 9H, C(CH$_3$)$_3$), 2.32 (s, 3H, 2-CH3), 2.15 (m), 2.50 (m(obscured) (2H, 7-H), 2.90-3.20 (m, 3H, 8-H, C≡CH), 3.95 (ABq, J=18.52 Hz, 2H, CH$_2$C≡C), 5.74 (t, J=7.70 Hz, 1H, 6-H), 6.80 (m, 2H, 3',5'-H), 7.48, 7.76 (2×s, each 1H, 5-H, 9-H), 7.68 (t, J=9.01 Hz, 6'-H), 12.10 (s, 1H, N$^3$-H); MS (ESI, m/z) 470 {(M+Na)$^+$, 55%}, 448 {M+H)$^+$, 70%}; FAB-HRMS; measured: 470.1840, calculated for C$_{26}$H$_{26}$FN$_3$O$_3$Na: 470.1856.

N-[(6RS)-2-Methyl-4-oxo-3,4,7,8-tetrahydro-6H-cyclopenta[g]quinazolin-6-yl]-N-(prop-2-ynyl)amino)-2-fluorobenzoic acid A solution of tert-butyl 4-{N-[(6RS)-2-methyl4-oxo-3,4,7,8-tetrahydro-6H-cyclopenta[g]quinazolin-6-yl]-N-(prop-2-ynyl)amino}-2-fluorobenzoate (0.061 g, 0.14 mmol) in dichloromethane (1 ml) and trifluoroacetic acid (2.4 ml) was stirred at room temperature for 1.5 hours, then the solvents were removed in vacuo. The residue was triturated with diethyl ether and the precipitate was collected by filtration, washed with diethyl ether and dried in vacuo over $P_2O_5$ to afford the desired compound as the trifluoroacetate salt (0.046 g). $^1$H-NMR (250 MHz, DMSO-$d_6$, TMS) 2.33 (s, 3H, 2-CH$_3$), 2.18 (m), 2.50 (m(obscured)) (2H, 7-H), 2.85-3.20 (m, 3H, 8-H, C≡CH), 3.95 (ABq, J=19.02 Hz, 2H, CH$_2$C≡C), 5.76 (t, J=7.95 Hz, 1H, 6-H), 6.80 (d, J=16.40 Hz, 1H, 3'-H), 6.84 (d, J=9.46 Hz, 1H, 5'-H), 7.48, 7.78 (2×s, each 1H, 5-H, 9-H) 7.74 (t, J=9.02 Hz, 6'-H). 12.14 (s, 1H, N$^3$-H); MS ESI, m/z) 783 {(2M+H)$^+$, 100%}, 392 {(M+H)$^+$, 55%}.

Tri-tert-butyl N-{N-{4[N-((6RS)-2-methoxymethyl-4-oxo-3,4,7,8-tetrahydro-6H-cyclopenta[g]quinazolin-6yl)N-(prop-2-ynyl)amino]-2-fluorobenzoyl}-L-γ-glutamyl}-D-glutamate To a solution of tri-tert-butyl L-γ-glutamyl-D-glutamate (V. Bavetsias et al, *J Med. Chem.* 1996, 39, 73-85; 0.066 g, 0.14 mmol) in anhydrous DMF (2.5 ml) was added 4-{N-[(6RS)-2-methyl4-oxo-3,4,7,8-tetrahydro-6H-cyclopenta[g]quinazolin-6-yl]-N-(prop-2-ynyl)amino}-2-fluorobenzoic acid trifluoroacetate salt (0.045 g, 0.11 mmol), followed by diethyl cyanophosphonate (0.051 g, 0.31 mmol) and triethylamine (0.032 g, 0.32 mmol). The reaction mixture was stirred at room temperature for 2.5 hours, then it was partitioned between ethyl acetate (150 ml) and water (100 ml). The aqueous layer was extracted with more ethyl acetate (100 ml). The combined organics were washed with 10% aqueous citric acid (2×50 ml), saturated sodium bicarbonate solution (2×50 ml), and brine (50 ml), then dried (Na$_2$SO$_4$), and concentrated in vacuo. Purification by column chromatography, on elution with 1% methanol in ethyl acetate, afforded a white solid: 0.077 g (67 %); m.p.>110° C. (softens); $^1$H-NMR (250 MHz, DMSO-$d_6$, TMS) 1.37, 1.38, 1.41 (3×s, 27H, 3×C(CH$_3$)$_3$), 1.60-2.35 (m, 9H, 2×β-CH$_2$, 2×γ-CH$_2$, 7-H), 2.32 (s, 3H, 2-CH$_3$), 2.52 (m obscured by DMSO peak, 1H, 7-H), 2.86-3.23 (m, 3H, C≡CH, 8-H), 3.97 (ABq, J=19.0 Hz, 2H, CH$_2$C≡C), 4.12, 4.30 (2×m, 2H, 2×α-CH), 5.74 (t, J=8.70 Hz, 1H, 6-H), 6.80 (d, J=14.20 Hz, 1H, 3'-H), 6.85 (d, J=8.07 Hz, 1H, 5'-H), 7.48 (s, 1H, 9-H), 7.58 (t, J=8.8 Hz, 1H, 6'-H), 7.78 (s, 1H, 5-H), 7.98 (t, J=6.42 Hz, 1H, CONH), 8.13 (d, J=7.4 Hz, 1H, CH$_2$CONH), 12.11 (s, 1H, N$^3$-H); (ESI, m/z) 818 {(M+H)$^+$, 100%}; Found C, 64.34; H, 7.09; N, 8.20; F, 2.22, C$_{44}$H$_{56}$FN$_5$O$_9$ requires C, 64.61; H, 6.90; N, 8.56; F, 2.32%.

N-{N-{4-[N-((6RS)-2methyl-4-oxo-3,4,7,8-tetrahydro-6H-cyclopenta[g]-quinazolin-6-yl)-N-(prop-2-ynyl)amino]-2-fluorobenzoyl}-L-γ-glutamyl}-D-glutamic acid A solution of tri-tert-butyl N-{N-{4-[N-((6RS)-2-methyl-4-oxo-3,4,7,8-tetrahydro-6H-cyclopenta[g]quinazolin-6-yl)-N-(prop-2-ynyl)amino]-2-fluorobenzoyl}-L-γ-glutamyl}-D-glutamate (0.066 g, 0.08 mmol) in trifluoroacetic acid (4.5 ml) was stirred at room temperature for 1 hour and 10 min with protection from the light. The solvent was then removed in vacuo and the residue was suspended in water (5 ml). The pH was adjusted to ~12 with 1N NaOH, then to ~4 with 1N hydrochloric acid. The white precipitate was collected by filtration and dried in vacuo over $P_2O_5$: 0.032 g (63%), m.p. 175° C. (dec); $^1$H-NMR (250 MHz, DMSO-$d_6$, TMS) 1.65-2.25 (m, 9H, 2×β-CH$_2$, 2×γ-CH$_2$, 7-H), 2.32 (s, 3H, 2-CH$_3$), 2.52 (m obscured by DMSO peak, 1H, 7-H), 2.90-3.22 (m, 3H, C≡CH, 8-H), 3.95 (ABq, J=19.15 Hz, 2H, CH$_2$C≡C), 4.18, 4.37 (2×m, 2H, 2×α-CH), 5.74 (t, J=8.30 Hz, 1H, 6-H), 6.81 (d, J=15.50 Hz, 1H, 3'-H), 6.85 (d, J=7.88 Hz, 1H, 5'-H), 7.48 (s, 1H, 9-H), 7.62 (t, J=8.8 Hz, 1H, 6'-H), 7.78 (s, 1H, 5-H), 7.97 (t, J=6.55 Hz, 1H, CONH), 8.12 (d, J=8.05 Hz, 1H, CH$_2$CONH), 12.11 (s, 1H, N$^3$-H); (ESI, m/z) 650 {(M+H)$^+$, 100%}; FAB-HRMS, measured: 672.2060; calculated for C$_{32}$H$_{32}$FN$_5$O$_9$Na: 672.2082.

EXAMPLE 3

Synthesis of CB300960 (N-methyl Derivative of CB300945)

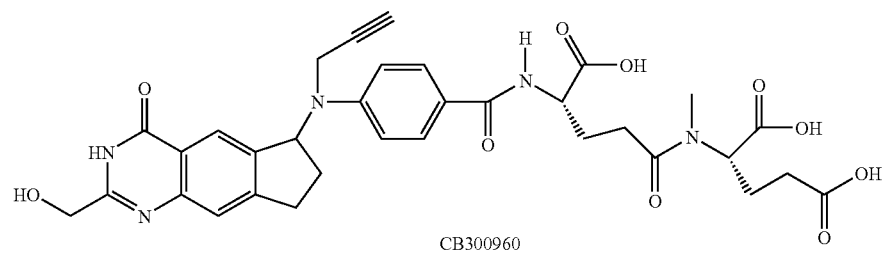

CB300960

4-{N-[(6RS)-2-Hydroxymethyl-4-oxo-3,4,7,8-tetrahydro-6H-cyclopenta[g]quinazolin-6yl]-N-(prop2-ynyl)amino}Benzoic Acid Method A: A solution of tert-butyl 4-{N-[(6RS)-2-(2,2-dimethylpropionyloxymethyl)-4-oxo-3,4,7,8-tetrahydro-6H-cyclopenta[g]quinazolin-6-yl]-N-(prop-2-ynyl)amino}benzoate (0.150 g, 0.28 mmol) in dichloromethane (2 ml) and trifluoroacetic acid (6 ml) was stirred at room temperature for 1 hour. The solvents were then removed in vacuo, and the residue was suspended in methanol (3 ml) and water (5 ml). The pH was adjusted to ~10 with 1N NaOH (1.1 ml), and the mixture was stirred at room temperature for 4 hours. The reaction mixture was diluted with water (5 ml) and the pH was adjusted to ~5 with 1N HCl. The solid was then collected by filtration, but $^1$H-NMR indicated no complete removal of the pivaloyl group. This solid was suspended into the filtrate and then 1N NaOH (0.9 ml, 0.9 mmol) was added (pH~12). The mixture was stirred at room temperature for 3.5 hours, then more 1N NaOH (0.2 ml) was added, and the mixture was stirred at room temperature for a further 0.5 hours. The pH was then adjusted to ~5.0 with 1N HCl. The off-white precipitate was collected by filtration, washed with water, and dried in vacuo over $P_2O_5$: 0.086 g, (79%); $^1$H-NMR (250 MHz, DMSO-$d_6$, TMS) 2.22 (m, 1H 7-CH), 2.90-3.30 (m, 3H, C≡CH, 8-H), 3.97 (ABq, J=18.6 Hz, 2H, $CH_2$C≡C), 4.37 (d, J=6.1 Hz, 2H, 2-$CH_2$), 5.56 (t, 1H, $CH_2$OH), 5.78 (t, J=7.51 Hz, 1H, 6-H), 7.03 (d, J=8.9 Hz, 2H, 3',5'-H), 7.55 (s, 1H, 9-H), 7.82 (m, 3H, 2',6'-H, 5-H), MS (ESI, m/z) 779 {(2M+H)$^+$, 100%}, 390 {(M+H)$^+$, 60%}.

Method B: A solution of tert-butyl 4-{N-[(6RS)-2-hydroxymethyl-4oxo-3,4,7,8-tetrahydro-6H-cyclopenta[g]quinazolin-6-yl]-N-(prop-2-ynyl)amino}-benzoate (0.050 g, 0.11 mmol) in dichloromethane (1 ml) and trifluoroacetic acid (2.4 ml) was stirred at room temperature for 1 hour. The solvents were then removed in vacuo, and the residue was triturated with diethyl ether. The off-white precipitate was collected by filtration, and washed with other to obtain the desired product as the trifluoroacetate salt: 0.044 g.

Tri-tert-butyl N-{N-{4-[N-((6RS)-2-hydroxymethyl-4-oxo-3,4,7,8-tetrahydro-6H-cyclopenta[g]quinazolin-6-yl]-N-(prop-2-ynyl)amino]benzoyl}-L-γ-glutamyl}-N-methyl-L-glutamate To a mixture of 4-{N-[(6RS)-2-hydroxymethyl-4-oxo-3,4,7,8-tetrahydro-6H-cyclopenta[g]quinazolin-6-yl]-N-(prop-2-ynyl)amino}benzoic acid (0.075 g, ~0.19 mmol), tri-tert-butyl L-γ-glutamyl-N-methyl-L-glutamate (V. Bavetsias et al., *J Med. Chem.*, 1997, 40, 1495-1510; 0.110 g, 0.24 mmol), and anhydrous DMF (2.0 ml) was added diethyl cyanophosphonate (0.036 g, 0.22 mmol) with the aid of anhydrous DMF (0.2 ml) followed by triethylamine (0.022 g, 0.22 mmol). The clear solution was stirred at room temperature for 1.5 hours, then it was partitioned between ethyl acetate (50 ml) and brine (40 ml). The aqueous layer was extracted with more ethyl acetate (2×50 ml). The combined organics were washed with 10% aqueous citric acid (40 ml), saturated sodium bicarbonate solution (40 ml), and brine (40 ml), dried ($Na_2SO_4$), and concentrated in vacuo. Purification by column chromatography, on elution with a gradient of methanol in dichloromethane (0 to 6%), afforded an off-white solid that was further purified by trituration with hexane/dichloromethane/diethyl ether: 0.062 g (40%); mp 116-120° C. (softens); $^1$H-NM (250 MHz, DMSO-$d_6$, TMS) 1.36, 1.37, 1.38, 1.41 (4×s, 27H, 3×C($CH_3$)$_3$), 1.70-2.35 (m) and 2.50 (m obscured by DMSO peak) (10H, 2×γ-$CH_2$, 2×γ-$CH_2$, 7-$CH_2$), 2.63, 2.82 (2×s, 3H, CONMe), 2.90-3.25 (m, 3H, C≡CH, 8-H), 3.97 (ABq, J=17.6 Hz, 2H, $CH_2$C≡C), 4.32 (m, 1H, glu α-CH), 4.38 (d, J=6.1 Hz, 2H, 2-$CH_2$), 4.50, 4.82 (2×dd, 1H, Meglu α-CH), 5.56 (t, J=6.9 Hz, 1H, $CH_2$OH), 5.78 (t, J=7.10 Hz, 1H, 6-H), 7.02 (d, J=8.6 Hz, 2H, 3',5'-H), 7.55 (s, 1H, 9-H), 7.78 (d, J=8.9 Hz, 2H, 2',6'-H), 7.82 (s, 1H, 5-H), 8.32 (m, 1H, CONH), 11.81 (s, 1H, $N^3$-H); MS (ESI, m/z) 830{(M+H)$^+$, 100%}.

N-{N-{4-[N-((6RS)-2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-N-methyl-L-glutamic acid A solution of tri-tert-butyl N-{N-{4-[N-((6RS)-2-hydroxymethyl-4-oxo-3,4,7,8-terahydro-6H-cyclopenta[g]quinazolin-6yl)-N-(prop-2-ynyl)amino]-benzoyl}-L-γ-glutamyl}-N-methyl-L-glutamate (0.060 g, 0.07 mmol) in trifluoroacetic acid (3.5 ml) was stirred at room temperature for 1 hour and 10 min with protection from the light. The solvent was then removed in vacuo and the residue was suspended in water (6 ml). The pH was adjusted to ~10 with 1N NaOH, then to ~4 with 1N hydrochloric acid. The white precipitate was collected by filtration, and dried in vacuo over $P_2O_5$: 0.035 g (77%), mp>165° C. (dec); $^1$H-NMR (250 MHz, DMSO-$d_6$, TMS) 1.80-2.35 (m) and 2.50 (m obscured by DMSO peak) (10H, 2×β-$CH_2$, 2×γ-$CH_2$, 7-$CH_2$), 2.66, 2.83 (2×s, 3H, CONMe), 2.90-3.25 (m, 3H, C≡CH, 8-H), 3.97 (ABq, J=18.4 Hz, 2H, $CH_2$C≡C), 4.32 (m obscured, 1H, glu α-CH), 4.38 (d, J=5.6 Hz, 2H, 2-$CH_2$), 4.55, 4.91 (2×dd, J=10.0, 4.5 Hz, 1H, Meglu α-CH), 5.56 (poorly resolved t, 1H, CH2OH), 5.77 (t, J=8.06 Hz, 1H, 6-H), 7.02 (d, J=7.8 Hz, 2H, 3',5-H), 7.55 (s, 1H, 9-H), 7.81 (d, J=10.1 Hz, 3H, 2',6'-H, 5-H), 8.32 (m, 1H, CONH), 11.82 (s, 1H, $N^3$-H); MS (ESI, m/z) 662 {(M+H)$^+$, 100%}; Found: C, 57.52; H, 5.52; N, 10.17; $C_{33}H_{35}N_5O_{10}$1.5 $H_2O$ requires: C, 57.55; H, 5.56; N, 10.17%.

EXAMPLE 4

In vitro Evaluation

The cyclopenta[g]quinazolines of the invention, particularly those with L-glu-γ-D-glu ligands, or modified ligands (e.g. CB300907 and CB300899) are potent inhibitors of TS (Kiapp 0.17 to 3 nM) and have very low affinities for the reduced-folate carrier (RFC) (Table 1). The affinities relative to folic acid (Table 1) varied little and were slightly lower than folic acid itself These properties did not necessarily predict for in vitro potency and selectivity for human cell lines overexpressing the α-FR. For example, CB300944, a 2-$NH_2$ analogue, has low potency and no selectivity for either A431-FBP or KB cells. The best compounds in this regard are the 2-$CH_3$ and 2-$CH_2$OH compounds. These were 150 to 4700-fold more active in A431-FBP cells compared with the A431 cells Similarly, when an excess of folic acid was added to block FR-mediated uptake in the A431-FBP cells, the difference ± folic acid was 100 to 4300-fold. In KB cells the difference ± folic acid was 73 to 2,100. It should be noted that all these experiments were performed in media containing 20 nM 5-formyl tetrahydrofolate (leucovorin; LV) as the folate source. This is in the physiological range of folate in human plasma. If experiments are done in low folate, 1 nM LV or lower (as many antifolate experiments in the literature are) then the degree of selectivity increases for several of the quinazoline-based compounds including CB3717.

Tables 4, 5, 6 and 7 show the structures of the compounds tested.

EXAMPLE 5

Formulation

The following illustrate representative pharmaceutical dosage forms containing a cyclopenta[g]quinazoline of formula (I), particularly in pharmaceutically acceptable salt form, for therapeutic or prophylactic use in humans:

| (a) | Tablet I | mg/tablet |
|---|---|---|
| | Cyclopenta[g]quinazoline salt | 100 |
| | Lactose Ph.Eur. | 182.75 |

|     |                                           |              |
| --- | ----------------------------------------- | ------------ |
|     | Croscarmellose sodium                     | 12.0         |
|     | Maize starch paste (5% w/v paste)         | 2.25         |
|     | Magnesium stearate                        | 3.0          |
| (b) | Tablet II                                 | mg/tablet    |
|     | Cyclopenta[g]quinazoline salt             | 50           |
|     | Lactose Ph.Eur.                           | 223.75       |
|     | Croscarmellose sodium                     | 6.0          |
|     | Maize starch                              | 15.0         |
|     | Polyvinylpyrrolidone (5% w/v paste)       | 2.25         |
|     | Magnesium stearate                        | 3.0          |
| (c) | Tablet III                                | mg/tablet    |
|     | Cyclopenta[g]quinazoline salt             | 1.0          |
|     | Lactose Ph.Eur.                           | 93.25        |
|     | Croscarmellose sodium                     | 4.0          |
|     | Maize starch paste (5% w/v paste)         | 0.75         |
|     | Magnesium stearate                        | 1.0          |
| (d) | Capsule                                   | mg/capsule   |
|     | Cyclopenta[g]quinazoline salt             | 10.0         |
|     | Lactose Ph.Eur.                           | 488.5        |
|     | Magnesium stearate                        | 1.5          |
| (e) | Injection I                               | (50 mg/ml)   |
|     | Cyclopenta[g]quinazoline salt             | 5.0% w/v     |
|     | 1M Sodium hydroxide solution              | 15.0% v/v    |
|     | 0.1M Hydrochloric acid                    |              |
|     | (to adjust pH to 7.6)                     |              |
|     | Polyethylene glycol 400                   | 4.5% w/v     |
|     | Water for injection to 100%               |              |
| (f) | Injection II                              | (10 mg/ml)   |
|     | Cyclopenta[g]quinazoline salt             | 1.0% w/v     |
|     | Sodium phosphate BP                       | 3.6% w/v     |
|     | 0.1M Sodium hydroxide solution            | 15.0% v/v    |
|     | Water for injection to 100%               |              |
| (g) | Injection III                             | (1 mg/ml. buffered to pH 6) |
|     | Cyclopenta[g]quinazoline salt             | 0.1% w/v     |
|     | Sodium phosphate BP                       | 2.26% w/v    |
|     | Citric acid                               | 0.38% w/v    |
|     | Polyethylene glycol 400                   | 3.5% w/v     |
|     | Water for injection to 100%               |              |

The above formulations may be prepared by conventional procedures well known in the pharmaceutical art. The tablets (a) to (c) may be enteric coated by conventional means, for example with a coating of cellulose acetate phthalate.

TABLE 1

In vitro properties of quinazolines and cyclopenta[g]quinazolines

|  |  |  | Inhibition of isolated L1210 | [1]Inhibition of $^3$H MTX uptake Ki (µM) | | [2]Inverse relative affinity for α-FR | |
| --- | --- | --- | --- | --- | --- | --- | --- |
|  |  | Ligand | TS, Kiapp (nM) | [3]L1210 | [4]W1L2 | [5]L1210-FBP | [6]A431-FBP |
| Comparative compounds | | | | | | | |
| *Raltitrexed | 2-CH$_3$ | L-Glu | 510 | 2.6, 2.3 | 0.61, 0.70 | 0.6 ± 0.1 | 0.24 ± 0.02 |
| *CB3717 | 2-NH$_2$ | L-Glu | 20 | 46 ± 17 | 20 ± 16 | 1.5 ± 0.12 | 1.2 ± 0.06 |
| *IC1198583 | 2-CH$_3$ | L-Glu | 31 | 2.6 ± 0.06 | 1.2, 1.0 | 0.80 ± 0.05 | |
| CB3900 | 2-CH$_3$, 7-CH$_3$ | L-Glu | 23 | 4.3, 4.7 | 1.3 | 0.30 ± 0.07 | |
| CB300464 (S) | 2-CH$_3$, cyclopentane | L-Glu | 3 | 9.1 ± 5.1 | 4.9 ± 2.3 | 0.44 ± 0.10 | 0.51 ± 0.0058 |
| CB300958 (R, S) | 2-NH$_2$, cyclopentane | L-glu | 0.75 | | | 0.73 ± 0.035 | 0.57 ± 0.059 |
| CB300959 (R, S) | 2-CH$_2$OH, cyclopentane | L-glu | 12 | | | 0.71 ± 0.012 | 0.57 ± 0.032 |
| ZD9331 | 2-CH$_3$, 7-CH$_3$, 2'F | L-Glu-γ-tet | 1.0 | 2.4 ± 1.0 | 0.76 ± 0.11 | 0.54 ± 0.1 | 0.30 ± 0.08 |
| CB30901 | 2-CH$_3$, 7-CH$_3$ | L-glu-γ-D-glu | 2.0 | 269 ± 162 | 83 | 0.31 ± 0.0089 | — |
| CB300944 (R, S) | 2-NH$_2$, cyclopentane | L-glu-γ-D-glu | 0.67 | >250 | >250, >250 | 0.73 ± 0.05 | 0.68 ± 0.10 |
| Compounds of the invention | | | | | | | |
| CB300638 (S) | 2-CH$_3$, cyclopentane | L-glu-γ-D-glu | 0.33 ± 0.16 | >250 | 115 ± 12 | 0.66 ± 0.08 | 0.53 ± 0.07 |
| CB300638 (R, S) | 2-CH$_3$, cyclopentane | L-glu-γ-D-glu | 0.42 | 166 ± 34 | 279 ± 146 | 0.60 ± 0.06 | 0.59 ± 0.03 |
| CB300947 (R, S) | 2-CH$_3$, 2'F, cyclopentane | L-glu-γ-D-glu | 0.46, 0.77 | >250 | 97,315 | 0.73 ± 0.01 | 0.58 ± 0.017 |
| CB300945 (S) | 2-CH$_2$OH, cyclopentane | L-glu-γ-D-glu | 1.9 | — | — | 0.70 ± 0.015 | 0.69 ± 0.05 |
| CB300945 (R, S) | 2-CH$_2$OH, cyclopentane | L-glu-γ-D-glu | 2.6, 3.3 | >250 | >250 | 0.73 ± 0.06 | 0.67 ± 0.11 |
| CB300907 (S) | 2-CH$_3$, cyclopentane | L-glu-γ-D-glu(α-tetrazole) | 0.16, 0.17 | 186 ± 121 | 142 ± 54 | 0.61 ± 0.07 | 0.58 ± 0.032 |

TABLE 1-continued

In vitro properties of quinazolines and cyclopenta[g]quinazolines

| | | Ligand | Inhibition of isolated L1210 TS, Kiapp (nM) | [1]Inhibition of $^3$H MTX uptake Ki (µM) | | [2]Inverse relative affinity for α-FR | |
|---|---|---|---|---|---|---|---|
| | | | | [3]L1210 | [4]W1L2 | [5]L1210-FBP | [6]A431-FBP |
| CB300899 (R, S) | 2-CH$_3$, cyclopentane | L-glu-NCH$_3$-L-glu | 0.78 | >250 | >250 | 0.62 ± 0.04 | 0.64 ± 0.046 |

*can be polyglutamated
[1]High Ki = low affinity for the reduced-folate carrier (RFC);
[2]High Inverse relative affinity = high affinity for the α-FR. Folic acid = 1;
[3]mouse L1210 tumor cells;
[4]human lymphoblastoid cells;
[5]L1210-FBP mouse tumor cells that overexpress the α-FR (Jansen et al., Cancer Res., 49, 2455-2459, 1989-later identified as L1210 origin: see correction in Cancer Res. 55, 1995);
[6]A431-FBP cells are human A431 tumor cells transfected with the α-FR (Bagnoli et al., Oncogene 19, 4754-4763, 2000)

TABLE 2

Activity of quinazolines and cyclopenta[g]quinazolines in human A431 and A431-FBP cell lines grown in 20 nM folate (R, S LV)

| | Inhibition of cell growth, IC$_{50}$, uM 20 nM LV | | Inhibition of cell growth, IC$_{50}$, uM 20 nM LV | |
|---|---|---|---|---|
| | A431 | [1]A431 + 1 µM FA (fold increased IC$_{50}$ in presence of folic acid) | [2]A431-FBP (fold increased sensitivity compared with A431) | [1]A431-FBP + 1 µM FA (fold increased IC$_{50}$ in presence of folic acid) |
| Comparative compounds | | | | |
| *Raltitrexed | 0.0034 ± 0.0016 | 0.0036 ± 0.0016 (1) | 0.00079 ± 0.00036 (4) | 0.0013 ± 0.00070 (2) |
| *CB3717 | 1.2 ± 0.63 | 1.4 ± 0.56 (1) | 0.26 ± 0.12 (4) | 0.45 ± 0.14 (2) |
| *ICI 198583 | 0.024 ± 0.004 | 0.026 ± 0.0038 (1) | 0.012 ± 0.005 (2) | 0.020 ± 0.0046 (2) |
| CB3900 | 2.2 ± 0.26 | 2.6 ± 0.92 (1) | 1.4 ± 0.36 (2) | 1.5 ± 0.29 (1) |
| CB300464 (S) | 0.76 ± 0.40 | 0.77 ± 0.41 (1) | 0.24 ± 0.13 (3) | 0.36 ± 0.17 (2) |
| CB300958 (R, S) | 23 | 23 (1) | 10 (2) | 20 (2) |
| CB300959 (R, S) | 4.2 | 5.8 (1) | 8.8 (0.5) | 18 (2) |
| ZD9331 | 0.082 ± 0.042 | 0.067 ± 0.029 (1) | 0.018 ± 0.0097 (4) | 0.034 ± 0.0087 (2) |
| CB30901 | 1.4 ± 0.70 | 1.1 ± 0.76 (1) | 0.21 ± 0.26 (5) | 0.47 ± 0.24 (2) |
| CB300944 (R, S) | 23, 27 | 22, 25 (1) | 8.3 ± 0.64 (3) | 7.1 ± 1.0 (1) |
| Compounds of the invention | | | | |
| CB300638 (S) | 0.81 ± 0.31 | 0.97 ± 0.58 (1) | 0.0030 ± 0.0021 (270) | 0.49 ± 0.17 (160) |
| CB300638 (R, S) | 1.4 ± 0.23 | 1.4 ± 0.25 (1) | 0.0065 ± 0.0001 (220) | 0.87 ± 0.29 (130) |
| CB300947 (R, S) | 1.4 ± 0.26 | 1.2 ± 0.51 (1) | 0.0094 ± 0.004 (150) | 0.93 ± 0.21 (100) |
| CB300945 (S) | 7.0 | 6.5 (1) | 0.0015 (4700) | 6.4 (4300) |
| CB300945 (R, S) | 9.8 ± 3.4 | 9.3 ± 3.5 (1) | 0.0021 ± 0.0011 (4700) | 6.5 ± 0.86 (3100) |
| CB300907 (S) | 1.4 ± 0.82 | 1.6 ± 1.1 (1) | 0.0026 ± 0.0018 (540) | 0.43 ± 0.18 (170) |
| CB300899 (R, S) | 2.2 ± 0.17 | 2.1 ± 0.058 (1) | 0.00092 ± 0.00012 (2400) | 1.9 ± 0.17 (2100) |
| CB300960 (R, S) | 4.5 | 4.3 (1) | 0.028 | 5.1 (180) |

*can be polyglutamated; FA = folic acid
[1]Folic acid is added in excess to compete with compounds for binding to the α-FR. Figures >1 in parentheses indicate α-FR-mediated uptake and growth inhibition;
[2]A431-FBP cells are transfected with the α-FR, and the figures in parentheses >1 indicate increased sensitivity relative to A431 cells and α-FR-mediated uptake. Higher numbers represent higher selectivity.

TABLE 3

Activity of quinazolines and oyclopenta[g]quinazolines in human KB cells grown in 20 nM folate (R, S LV)

| | Inhibition of cell growth, $IC_{50}$, $\mu M$ 20 nM LV | |
|---|---|---|
| | [1]KB | [2]KB + 1 $\mu M$ FA (fold increased $IC_{50}$ in presence of folic acid) |
| Comparative compounds | | |
| Raltitrexed | 0.0011 ± 0.00071 | 0.0012 ± 0.00059 (1) |
| CB3717 | 0.007 ± 0.002 | 0.58 ± 0.20 (80) |
| ICI 198583 | 0.002 ± 0.0004 | 0.02 ± 0.002 (10) |
| CB3900 | 0.13 ± 0.006 | 0.31 ± 0.04 (2) |
| CB300464 (S) | 0.009 ± 0.0004 | 0.21 ± 0.01 (23) |
| CB300958 (R, S) | 8.4, 6.8 | 26, 15 (3) |
| CB300959 (R, S) | 0.42, 0.50 | 5.8, 4.8 (11) |
| ZD9331 | 0.0036 ± 0.0021 | 0.01 ± 0.005 (3) |
| CB30901 | 0.010 ± 0.0056 | 0.21 ± 0.023 (21) |
| CB300944 (R, S) | 19 ± 0.58 | 19 ± 1.2 (1) |
| Compounds of the invention | | |
| CB300638 (S) | 0.0036 ± 0.0015 | 0.39 ± 0.18 (110) |
| CB300638 (R, S) | 0.0053 ± 0.0025 | 0.76 ± 0.17 (140) |
| CB300947 (R, S) | 0.008 ± 0.001 | 0.58 ± 0.03 (73) |
| CB300945 (S) | 0.0027 ± 0.0015 | 4.8 ± 0.75 (1800) |
| CB300945 (R, S) | 0.0034 ± 0.0009 | 7.3 ± 2.0 (2100) |
| CB300907 (S) | 0.0062 ± 0.003 | 0.49 ± 0.14 (79) |
| CB300899 (R, S) | 0.0051 ± 0.00031 | 2.2 ± 0.40 (430) |

[1]KB cells consitutively overexpress the $\alpha$-FR
[2]Folic acid is added in excess to compete with compounds for binding to the $\alpha$-FR. Figures >1 in parentheses indicate $\alpha$-FR-mediated uptake and growth inhibition. Higher numbers represent a high degree of $\alpha$-FR-mediated uptake

TABLE 4

Structures of the compounds tested-Comparative compounds

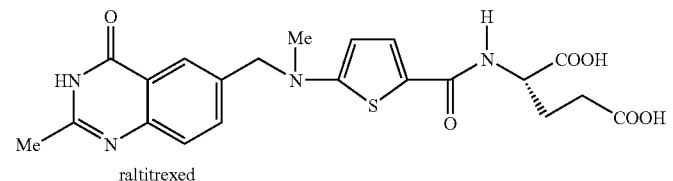

raltitrexed

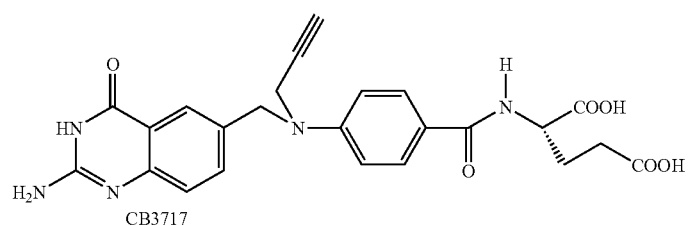

CB3717

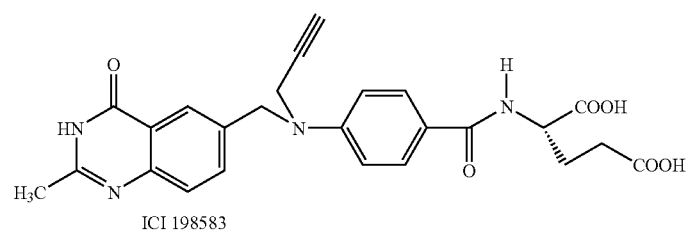

ICI 198583

TABLE 4-continued
Structures of the compounds tested-Comparative compounds
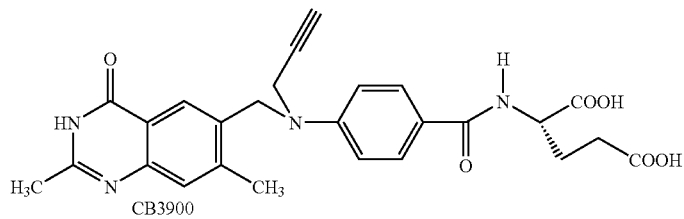
CB3900
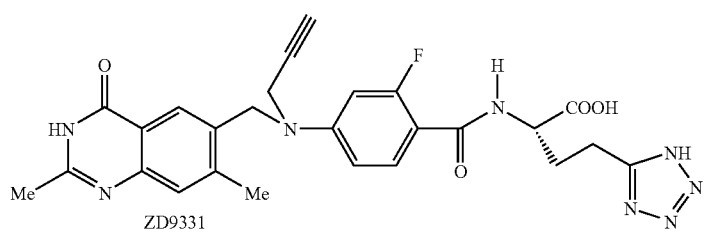
ZD9331
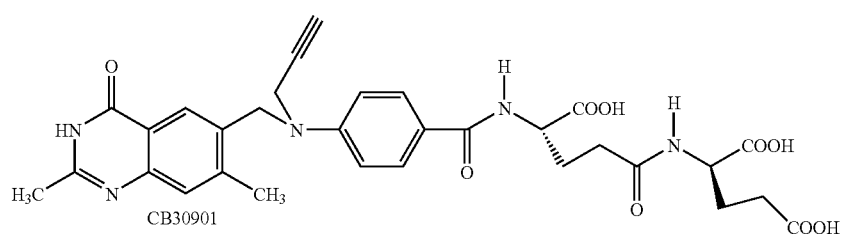
CB30901
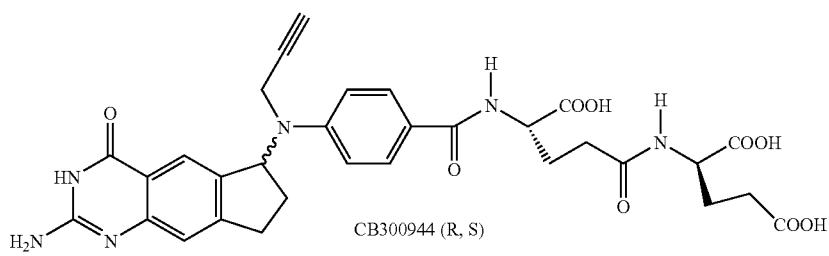
CB300944 (R, S)
TABLE 5
Structures of the compounds tested-Comparative compounds
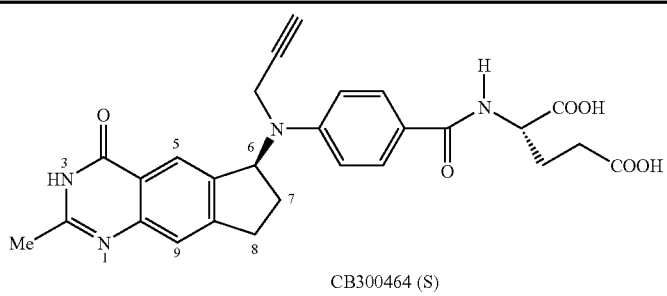
CB300464 (S)

TABLE 5-continued
Structures of the compounds tested-Comparative compounds
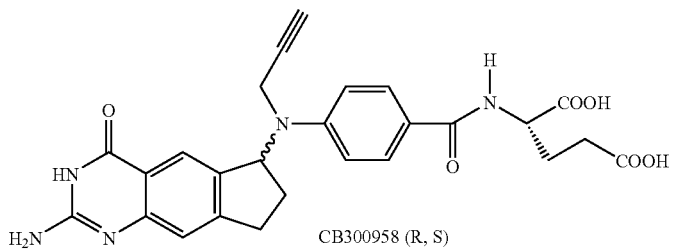
CB300958 (R, S)
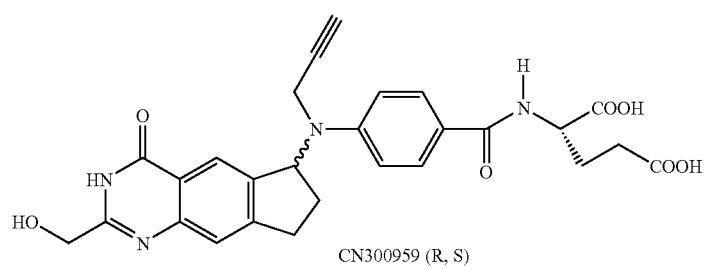
CN300959 (R, S)
TABLE 6
Structures of the compounds tested-Compounds of the invention
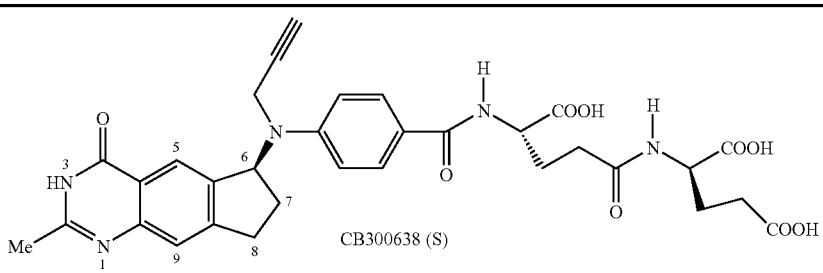
CB300638 (S)
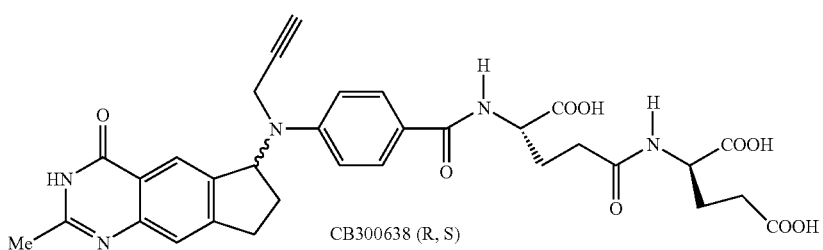
CB300638 (R, S)
TABLE 7
Structures of the compounds tested-Compounds of the invention
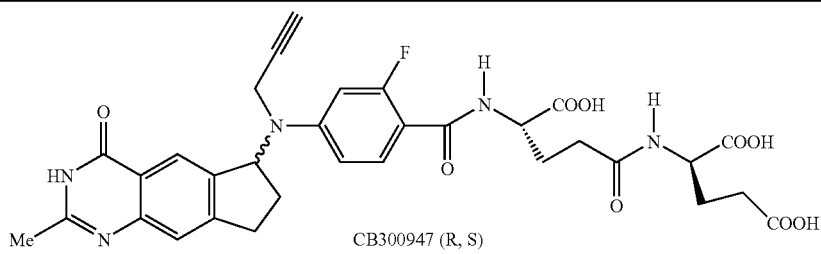
CB300947 (R, S)

TABLE 7-continued

Structures of the compounds tested-Compounds of the invention

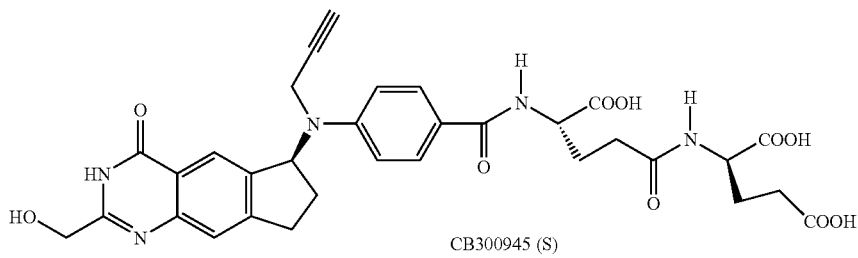

CB300945 (S)

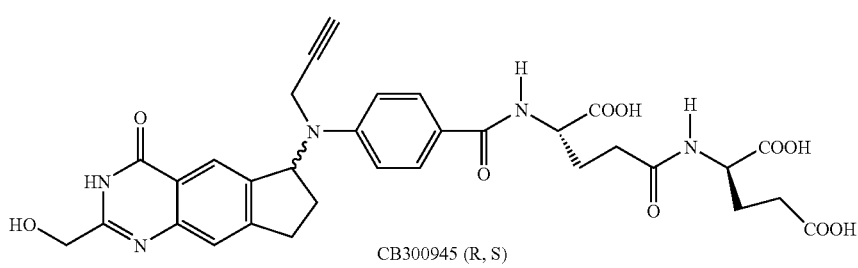

CB300945 (R, S)

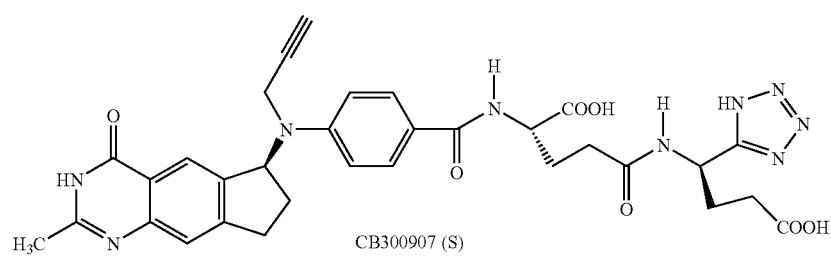

CB300907 (S)

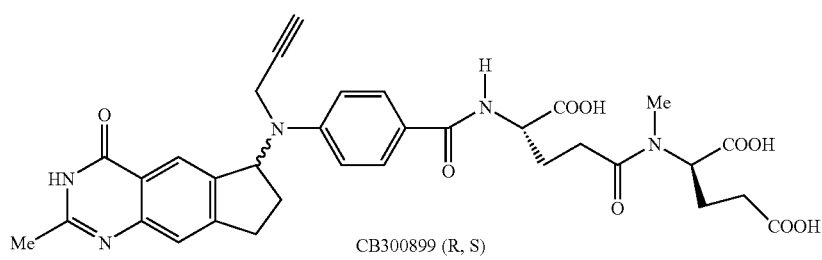

CB300899 (R, S)

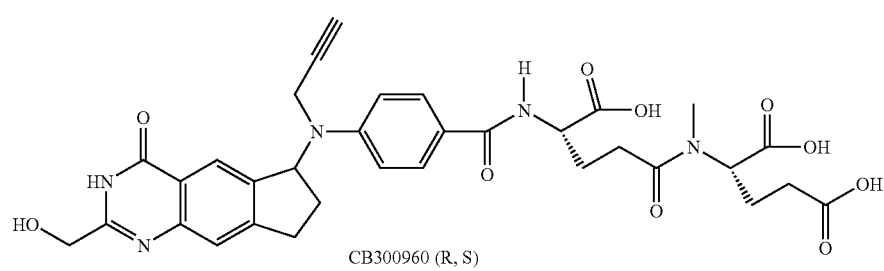

CB300960 (R, S)

The invention claimed is:

1. A method for selectively aiding regression and palliation of a solid tumour over-expressing the α-isoform of the folate receptor in a patient in need of such treatment, which method comprises administering to said patient an effective amount of a cyclopenta[g]quinazoline of the formula (I):

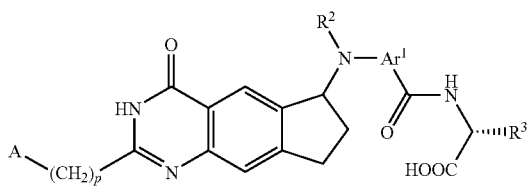
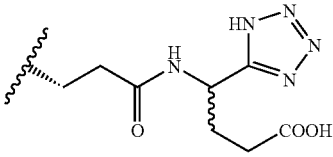

wherein:
 A is OH;
 p is 1;
 $R^2$ is prop-2-ynyl;
 $Ar^1$ is 1,4-phenylene or 1,4-phenylene having a 2-fluoro; and
 $R^3$ is of formula:

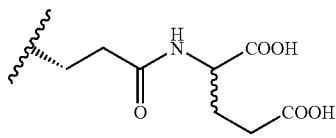

or $R^3$ is the corresponding N-methyl derivative of formula:

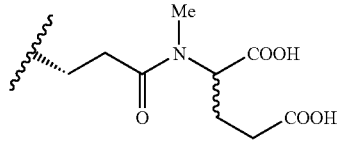

or $R^3$ is the corresponding tetrazol-5-yl derivative of formula:

the compound (I) optionally being in the form of a pharmaceutically acceptable salt.

2. The method as claimed in claim 1 wherein the cyclopenta[g]quinazoline of formula (I) is:

N-{N-{4-[N-(2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid; or N-{N-{4-[N-(2-hydroxymethyl-4-oxo-3,4,7,8-tetrahydro-6H-cycropenta[g]quinazolin-6-yl)-N-(prop-2-ynyl)amino]benzoyl}-L-γ-glutamyl}-N-methyl-L-glutamic acid;

or a pharmaceutically acceptable salt thereof.

3. The method according to claim 1 wherein the cyclopenta[g]quinazoline of formula (I) is administered together with a pharmaceutically acceptable diluent or carrier.

4. The method according to claim 1 wherein the solid tumor is a carcinoma of ovarian origin.

\* \* \* \* \*

UNITED STATES PATENT AND TRADEMARK OFFICE
CERTIFICATE OF CORRECTION

PATENT NO. : 7,528,141 B2
APPLICATION NO. : 10/487874
DATED : May 5, 2009
INVENTOR(S) : Bavetsias et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by (34) days Delete the phrase "by (34) days" and insert -- by 76 days --

Signed and Sealed this

First Day of June, 2010

David J. Kappos
*Director of the United States Patent and Trademark Office*